(12) United States Patent
Tew et al.

(10) Patent No.: US 8,329,927 B2
(45) Date of Patent: Dec. 11, 2012

(54) WATER-SOLUBLE AND WATER-INSOLUBLE, RING OPENING METATHESIS POLYMERIZATION PRODUCTS, MONOMERS AND RELATED METHODS

(75) Inventors: Gregory N. Tew, Amherst, MA (US); Ahmad Emad-Eldin Madkour, Amherst, MA (US); Sterling Fitzgerald Alfred, Durham, NC (US); Paralee Patten King, Princeton, MA (US); Semra Colak, Amherst, MA (US)

(73) Assignee: University of Massachusetts, Boston, MA (US)

( * ) Notice: Subject to any disclaimer, the term of this patent is extended or adjusted under 35 U.S.C. 154(b) by 1115 days.

(21) Appl. No.: 12/234,180

(22) Filed: Sep. 19, 2008

(65) Prior Publication Data
US 2009/0082524 A1   Mar. 26, 2009

Related U.S. Application Data

(60) Provisional application No. 60/994,550, filed on Sep. 20, 2007.

(51) Int. Cl.
*C07D 311/00* (2006.01)
*C07C 69/753* (2006.01)
(52) U.S. Cl. ........................... 549/397; 560/120
(58) Field of Classification Search ............... 549/397; 560/120
See application file for complete search history.

(56) References Cited

OTHER PUBLICATIONS

PCT International Search Report, PCT/US2008/077071.
PCT Written Opinion of the International Searching Authority, PCT/US2008/077071.

*Primary Examiner* — Kelechi Egwim
(74) *Attorney, Agent, or Firm* — Milstein Zhang & Wu LLC

(57) ABSTRACT

The invention provides certain novel water-soluble and water-insoluble monomers for ring opening metathesis polymerization and novel polymers, compositions and products, and related methods thereof.

14 Claims, 9 Drawing Sheets

Examples of end-functionalized poly(ethylenoxide) monomers synthesized and polymerized.

FIG. 1. Examples of end-functionalized poly(ethylenoxide) monomers synthesized and polymerized.
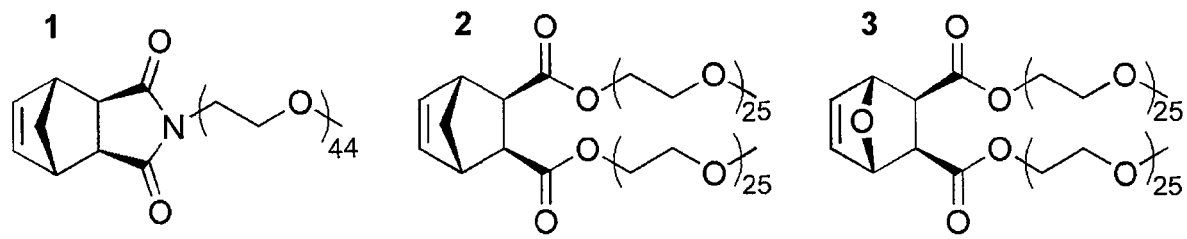

FIG. 2. Maldi-TOF spectrum of norbornene macromonomer 2 (Matrix : 2, 4-dihydroxybenzoic acid, counter ion: Na).
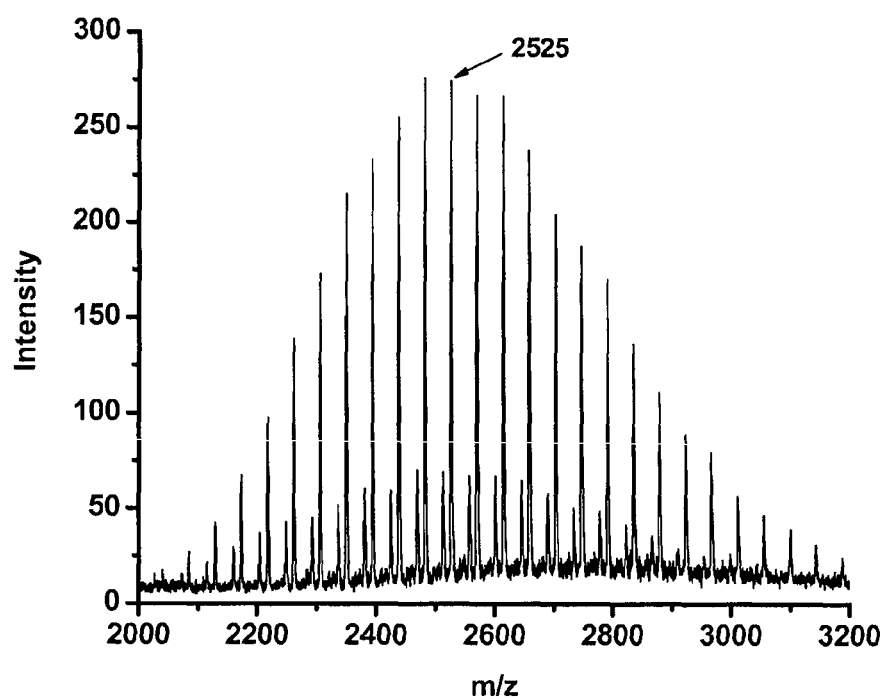

FIG. 3. GPC trace of macromonomer 2 (left) and its intermediate (right)
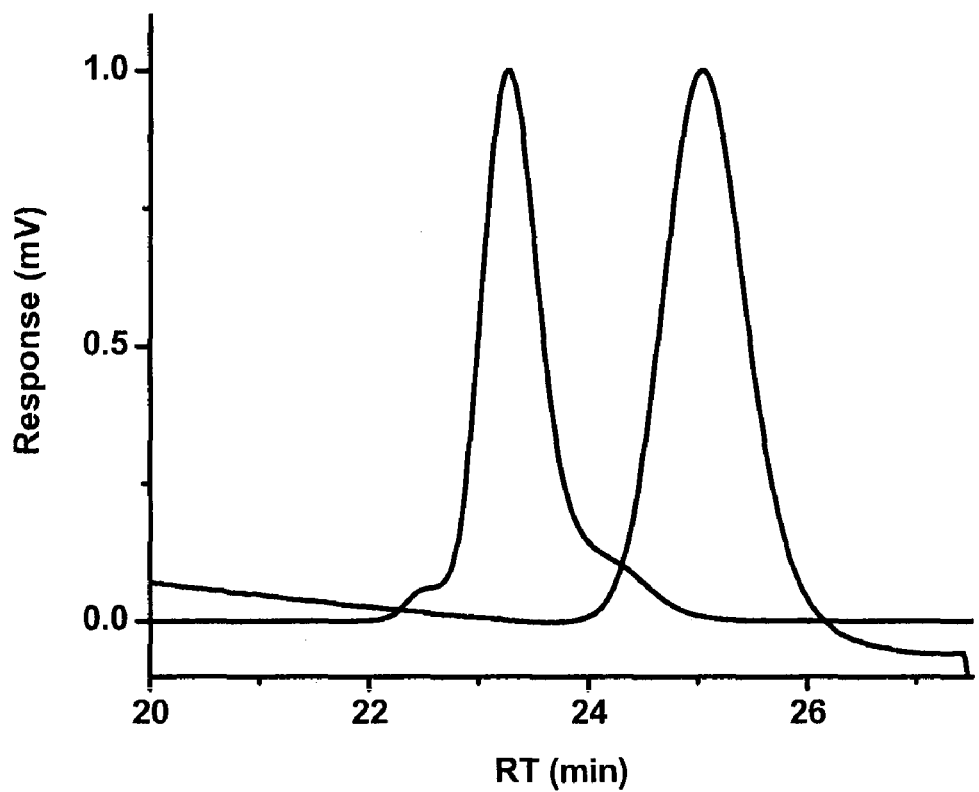

FIG. 4. $^1$H-NMR (300 MHz, CDCl$_3$) spectrum of the intermediate (bottom) and macromonomer 2 (top) in CDCl$_3$
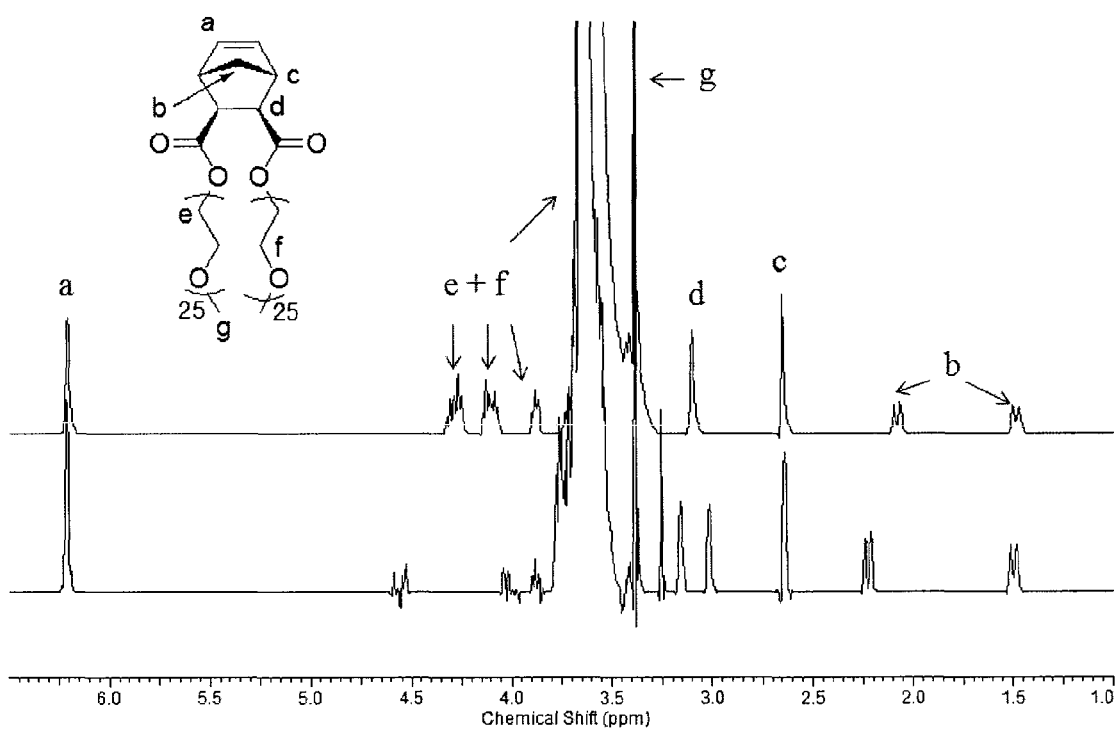

FIG. 5. GPC traces for polymers 1 (a, in DMF) 2c (b, in THF)
(a)
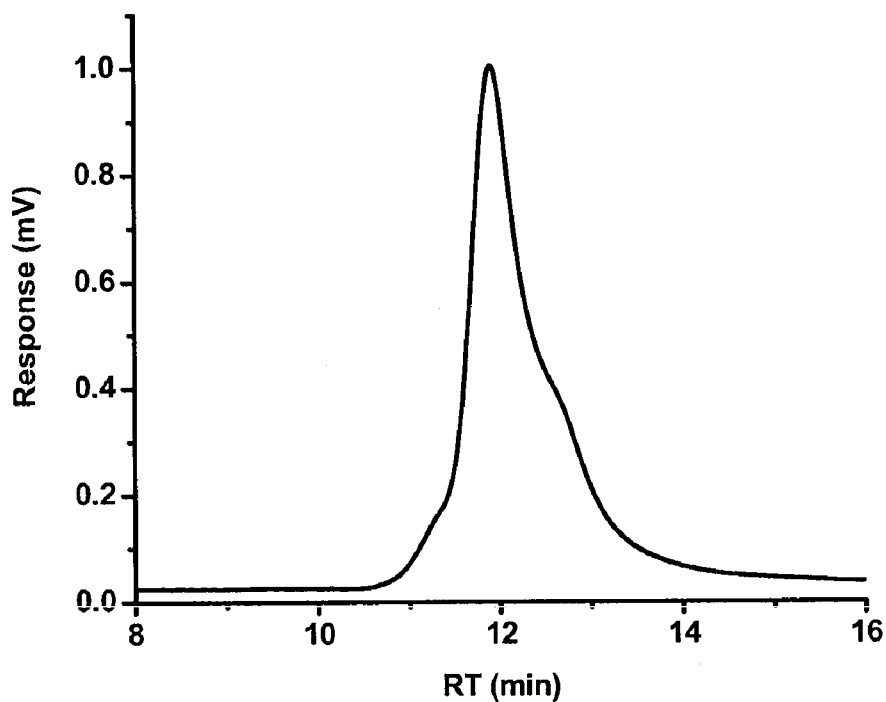
(b)
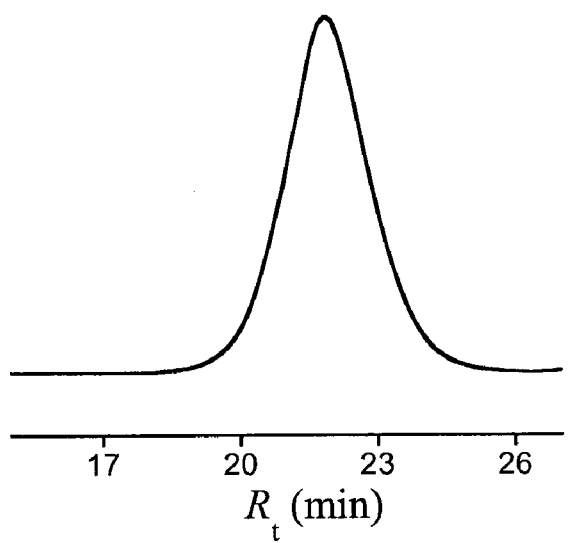

FIG. 6. Dynamic Light scattering results on 2b (a) and 3a (b): Field correlation function $g^1$ (q, τ) (dots) and relaxation time distribution function (diamonds) at a scattering angle of 30°.
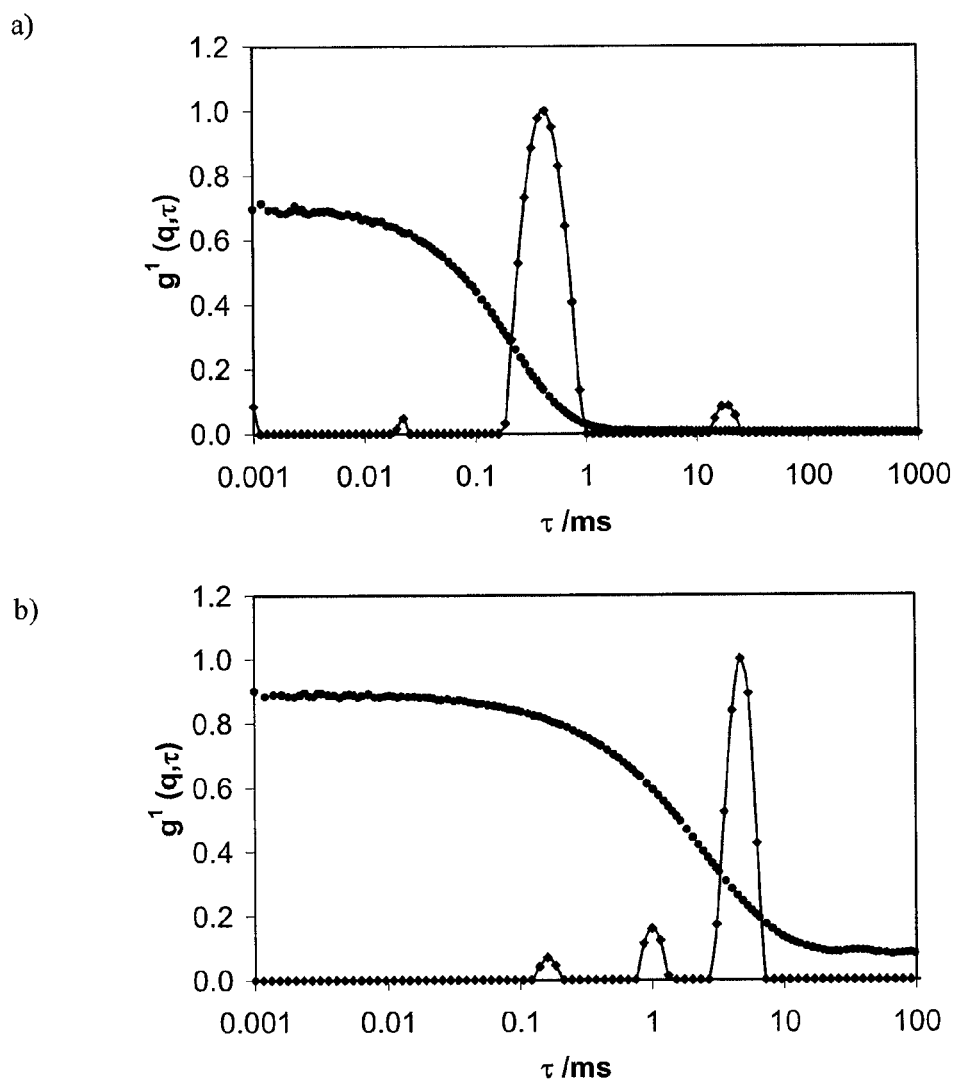

FIG. 7. OxyNorbornene-Diamine Swelling Data
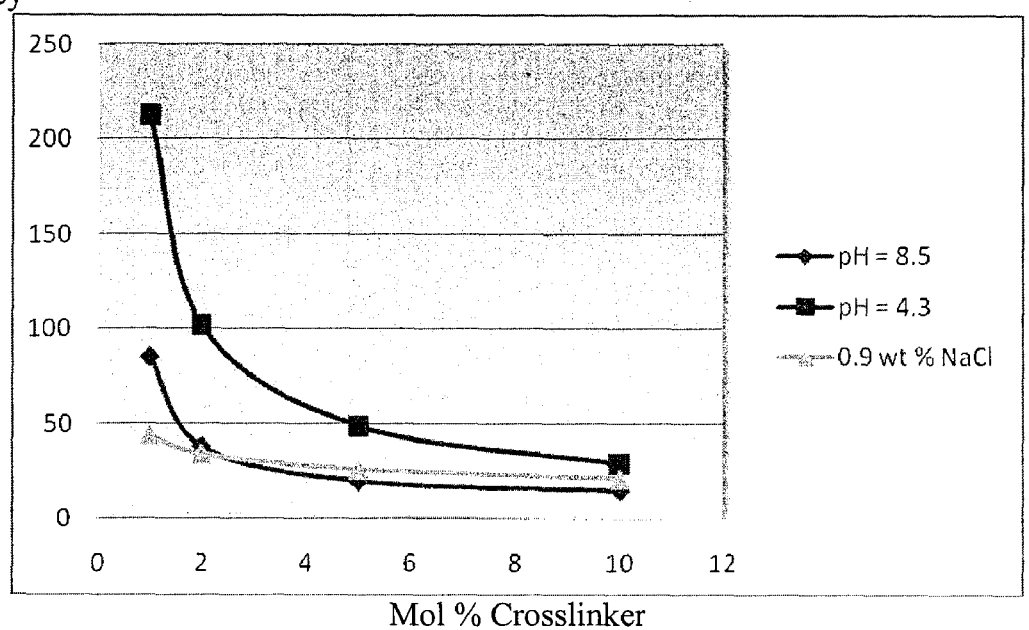

FIG. 8. OxyNorbornene-Diacid Swelling Data
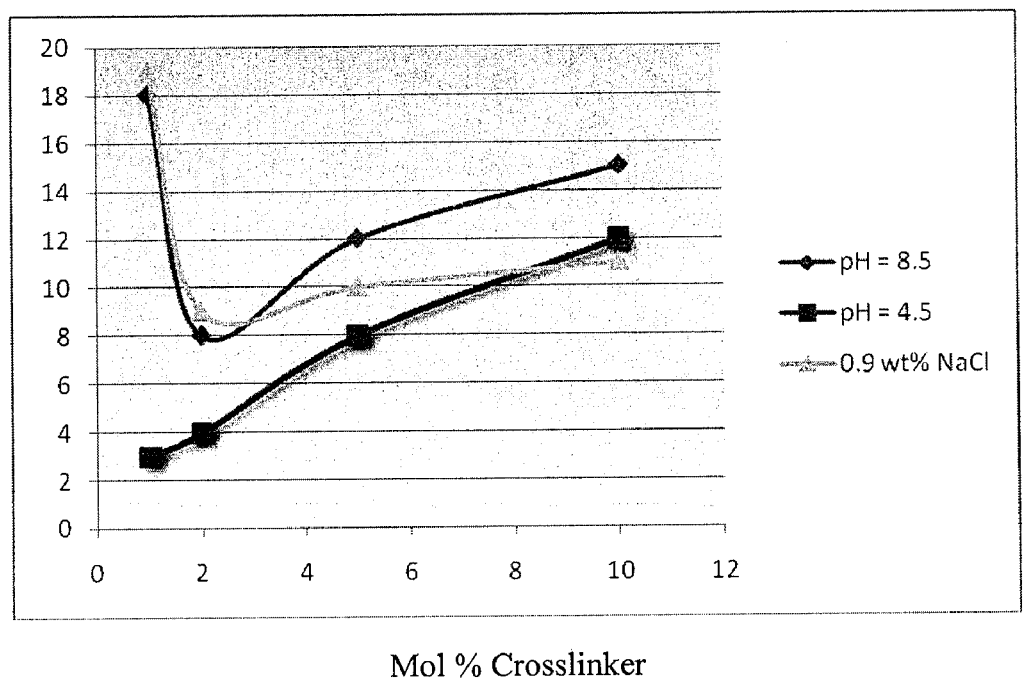

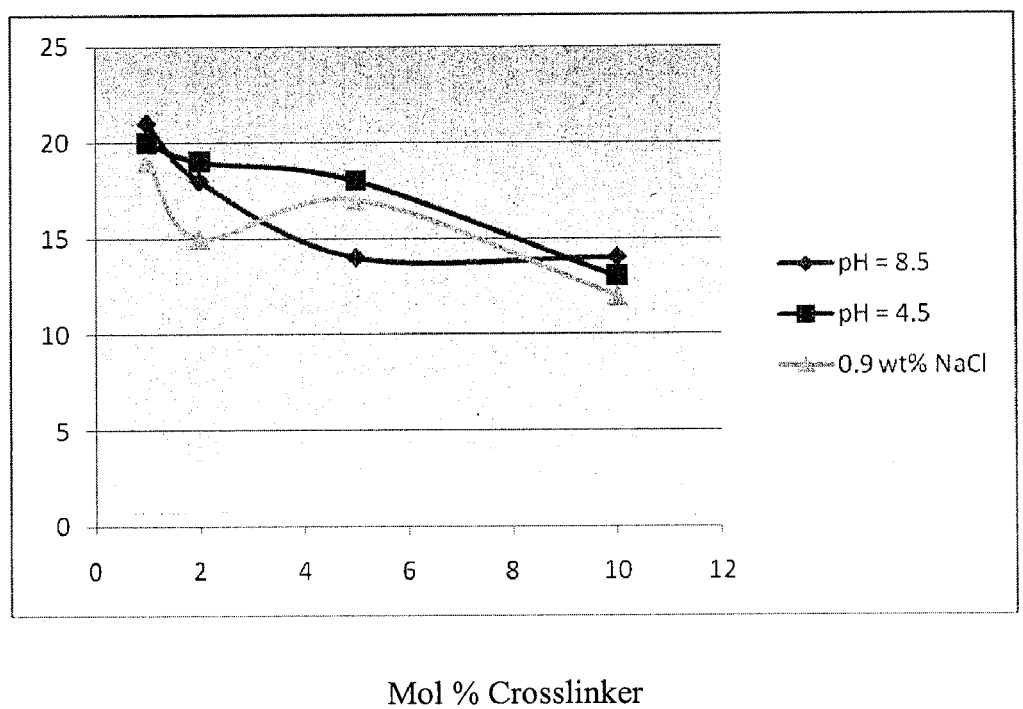
FIG. 9. OxyNorbornene-Tetrahydroxy Swelling Data

WATER-SOLUBLE AND WATER-INSOLUBLE, RING OPENING METATHESIS POLYMERIZATION PRODUCTS, MONOMERS AND RELATED METHODS

RELATED APPLICATIONS

This application claims the benefit of U.S. provisional patent application Ser. No. 60/994,550, which was filed in the U.S. Patent and Trademark Office on Sep. 19, 2007, the contents of which is incorporated by reference herein in its entirety.

GOVERNMENT RIGHTS

The United States Government has certain rights to the invention pursuant to Grant No. DMR-0213695 from the National Science Foundation to the University of Massachusetts.

FIELD OF THE INVENTION

The invention relates to water-soluble and water-insoluble monomers and polymers. More particularly, the invention relates to certain water-soluble and water-insoluble, ring opening metathesis polymerization monomers and, polymers, compositions and products comprising same, and related methods.

BACKGROUND OF THE INVENTION

One method that can be used to achieve control of a polymer's molecular weight (MW) and polydispersity is through ring opening metathesis polymerization (ROMP). ROMP is valuable where undesirable termination and chain transfer reactions are either absent or insignificant and polymerization rates are usually very rapid with high MW polymers approaching 100 kDa often obtained within minutes.

Additionally, copolymers, such as di-block and tri-block co-polymers and gradient co-polymers, can be easily made by sequential addition of another monomer(s) after consumption of the previous monomer. Ruthenium (Ru)-based catalysts allow the polymerization of strained unsaturated cyclic monomers with numerous functionalities. Some of the most commonly polymerized monomers are norbornene and its derivatives. Polymerization over a wide range of functional groups may be easily-controlled. A concurrent, related interest for aqueous polymer systems is the use of poly(ethylene oxide) (or "PEO") containing monomers. Such polymers may be used in various applications such as biomedical, water treatment, wound healing and other end-use applications where water-soluble polymers and/or hydrogels are useful.

Despite the wide spread use of some PEO functionalized polymers, little is known on PEO-functionalized norbornenes. No PEO water-soluble norbornene or other ROMP monomers are believed to have been prepared. Anionic polymerization of ethylene oxide from norbornene monomers containing a primary alcohol functional group was reported. This PEO-functionalized macromonomer was then polymerized using a Schrock-type catalyst to obtain polymers with high MWs (47-117 kDa) and polydispersity index (PDI) around 1.1 (for only one polymer). More recently, another approach involved the attachment of short EO units (n=4) to norbornene monomers. These monomers were further functionalized by reacting the hydroxyl end group of the EO with 2-bromopropionyl bromide to incorporate atom transfer radical polymerization (ATRP) initiators in the side chains. See, e.g., 15 Héroguez, et al. *Macromolecules* 1997, 30, 4791; Chemtob, et al. *Macromolecules* 2002, 35, 9262; Chemtob, et al. *Macromolecules* 2004, 42, 2705; Quémener, et al. *Macromolecules* 2006, 39, 5589; Héroguez, et al. *Macromolecules*, 1996, 29, 4459.

SUMMARY OF THE INVENTION

The invention is based in part on the unexpected discovery of novel monomers suitable for ROMP, novel polymers, and related compositions, products and methods thereof that exhibit improved or superior characteristics having great potential for various applications. More particularly, for example, one aspect of the invention provides novel PEO-functionalized norbornene monomers that undergo ROMP to produce novel water-soluble and water-insoluble polymers having desired properties, e.g., narrow polydispersity of 1.0 to 1.5 and molecular weight between 50 kDa and 100 kDa. Water-soluble polymers, especially made via ROMP, are of great interest and have potential in many areas, such as biomaterials, dispersants, flocculants, and other soft material applications.

In one aspect, the invention is generally related to a substantially water-soluble monomer, or a monomer convertible to be substantially water-soluble, that is suitable for polymerization. In certain preferred embodiments, the monomer is suitable for polymerization conducted under aqueous reaction conditions, for example, wherein the polymerization is a ring opening metathesis polymerization catalyzed by a suitable catalyst. Suitable catalysts, for example, include various Ru-based catalysts such as those selected from the first generation of Grubb's catalysts, the second generation of Grubb's catalysts, the third generation of Grubb's catalysts and others modified to be water soluble.

In certain preferred embodiments, the monomer is a norbornene functionalized with poly(ethylene oxide) or an oxanorbornene functionalized with poly(ethylene oxide). For example, the monomer is of Formula I:

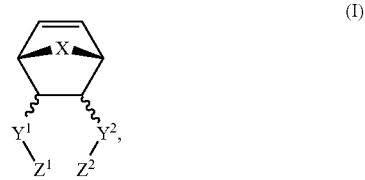

wherein
X is O, CH$_2$ or substituted CH$_2$;
Y$^1$, Y$^2$ are each independently carbonyl, (C$_1$-C$_4$) alkylene, substituted (C$_1$-C$_4$) alkylene; and
Z$^1$, Z$^2$ are each independently —OH, —OR$_z$, alkyl, —NR$_z$, substituted alkyl, aryl, substituted aryl,
wherein
R$_z$ is an alkyl, substituted alkyl, aryl, substituted aryl, poly (ethylene oxide),

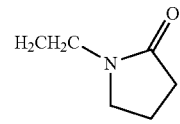

wherein $Z^1$ and $Z^2$ may together form a 5-, 6-, or 7-membered ring with the proviso that when each $Y^1$ and $Y^2$ is carbonyl, the formed ring is not a 5-membered ring with a $Y^1$ and $Y^2$ joined by a N atom.

In certain preferred embodiments, each of $Y^1$ and $Y^2$ is a carbonyl group. In certain detailed embodiments, each of $Z^1$ and $Z^2$ is independently —$OR_z$,
wherein
$R_z$ is
n is an integer from 1 to 50.

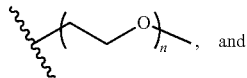

In certain embodiments, X is O. In certain other embodiments, X is $CH_2$ or substituted $CH_2$.

In another aspect, the invention generally relates to a polymer comprising a monomer of Formula Ia:

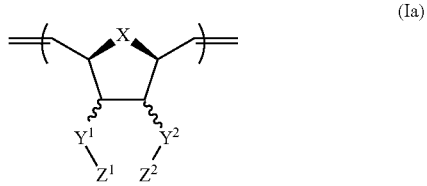

wherein
X is O, $CH_2$ or substituted $CH_2$;
$Y^1$, $Y^2$ are each independently carbonyl, ($C_1$-$C_4$) alkylene, substituted ($C_1$-$C_4$) alkylene; and
$Z^1$, $Z^2$ are each independently —OH, —$OR_z$, alkyl, —$NR_z$, substituted alkyl, aryl, substituted aryl,
wherein
$R_z$ is an alkyl, substituted alkyl, aryl, substituted aryl, poly(ethylene oxide).

In certain preferred embodiments, each of $Y^1$ and $Y^2$ is a carbonyl group. In certain embodiments, each of $Z^1$ and $Z^2$ is independently —$OR_z$,
wherein
$R_z$ is

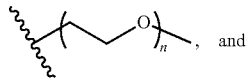

n is an integer from about 1 to about 50.

In yet another aspect, the invention generally relates to a method for producing a polymer, comprising contacting water-soluble monomers with one or more catalysts under conditions that allow polymerization of the monomers to obtain water-soluble polymers.

In certain preferred embodiments, the polymerization is by way of a ring opening metathesis polymerization.

The invention also encompasses compositions and articles of manufacture comprising the monomers or polymers of the invention. For example, the compositions or articles may be made with a cross-linked polymer of the invention. The swelling ratio of polymers, for example, may be from about 30 to about 150, from about 30 to about 100, or from about 30 to about 50. In certain other embodiments, the polymer has a swelling ratio of less than about 3.0, less than about 1.0, less than about 0.5, or less than about 0.2.

An example of such articles having polymers of the invention is a contact lens or material used thereof.

DEFINITIONS

Definitions of specific functional groups and chemical terms are described in more detail below. General principles of organic chemistry, as well as specific functional moieties and reactivity, are described in "Organic Chemistry", Thomas Sorrell, University Science Books, Sausalito: 1999.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are contemplated by the present invention. Those of ordinary skill in the art will readily appreciate that analogous ratios are contemplated for more complex isomer mixtures.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic methods well known in the art, and subsequent recovery of the pure enantiomers.

Given the benefit of this disclosure, one of ordinary skill in the art will appreciate that synthetic methods, as described herein, may utilize a variety of protecting groups. By the term "protecting group", as used herein, it is meant that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group should be selectively removable in good yield by preferably readily available, non-toxic reagents that do not attack the other functional groups; the protecting group forms an easily separable derivative (more preferably without the generation of new stereogenic centers); and the protecting group has a minimum of additional functionality to avoid further sites of reaction. Oxygen, sulfur, nitrogen, and carbon protecting groups may be utilized. Examples of a variety of protecting groups can be found in Protective Groups in Organic Synthesis, Third Ed. Greene, T. W. and Wuts, P. G., Eds., John Wiley & Sons, New York: 1999.

It will be appreciated that the compounds, as described herein, may be substituted with any number of substituents or functional moieties.

As used herein, ($C_x$-$C_y$) refers to groups that have from x to y (inclusive) carbon atoms. Therefore, for example, $C_1$-$C_6$ refers to groups that have 1, 2, 3, 4, 5, or 6 carbon atoms, which encompass $C_1$-$C_2$, $C_1$-$C_3$, $C_1$-$C_4$, $C_1$-$C_5$, $C_2$-$C_3$, $C_2$-$C_4$, $C_2$-$C_5$, $C_2$-$C_6$, and all like combinations. ($C_1$-$C_{20}$) and the likes similarly encompass the various combinations between 1 and 20 (inclusive) carbon atoms, such as ($C_1$-$C_6$), ($C_1$-$C_{12}$) and ($C_3$-$C_{12}$).

As used herein, the term "($C_x$-$C_y$)alkyl" refers to a saturated linear or branched free radical consisting essentially of x to y carbon atoms, wherein x is an integer from 1 to about 10 and y is an integer from about 2 to about 20. Exemplary ($C_x$-$C_y$)alkyl groups include "($C_1$-$C_{20}$)alkyl," which refers to a saturated linear or branched free radical consisting essentially of 1 to 20 carbon atoms and a corresponding number of hydrogen atoms. Exemplary ($C_1$-$C_{20}$)alkyl groups include methyl, ethyl, n-propyl, isopropyl, n-butyl, isobutyl, dodecanyl, etc. Of course, other ($C_1$-$C_{20}$)alkyl groups will be readily apparent to those of skill in the art given the benefit of the present disclosure.

As used herein, the term "($C_x$-$C_y$)cycloalkyl" refers to a nonaromatic saturated free radical forming at least one ring consisting essentially of x to y carbon atoms, wherein x is an integer from 1 to about 10 and y is an integer from about 2 to about 20. As such, ($C_x$-$C_y$)cycloalkyl groups may be monocyclic or multicyclic. Individual rings of such multicyclic cycloalkyl groups can have different connectivities, e.g., fused, bridged, spiro, etc. in addition to covalent bond substitution. Exemplary ($C_x$-$C_y$)cycloalkyl groups include "($C_3$-$C_{10}$)cycloalkyl," which refers to a nonaromatic saturated free radical forming at least one ring consisting essentially of 3 to 10 carbon atoms and a corresponding number of hydrogen atoms. As such, ($C_3$-$C_{10}$)cycloalkyl groups can be monocyclic or multicyclic. Individual rings of such multicyclic cycloalkyl groups can have different connectivities, e.g., fused, bridged, spiro, etc. in addition to covalent bond substitution. Exemplary ($C_3$-$C_{10}$)cycloalkyl groups include cyclopropyl, cyclobutyl, cyclopentyl, cyclohexyl, norbomanyl, bicyclo[3.2.1]octanyl, octahydro-pentalenyl, spiro[4.5]decanyl, cyclopropyl substituted with cyclobutyl, cyclobutyl substituted with cyclopentyl, cyclohexyl substituted with cyclopropyl, etc. Of course, other ($C_3$-$C_{10}$)cycloalkyl groups will be readily apparent to those of skill in the art given the benefit of the present disclosure.

As used herein, the term "($C_x$-$C_y$)heterocycloalkyl" refers to a nonaromatic free radical having x+1 to Y+1 atoms (i.e., ring atoms) that form at least one ring, wherein x to y of the ring atoms are carbon and the remaining ring atom(s) (i.e., hetero ring atom(s)) is selected from the group consisting of nitrogen, sulfur, and oxygen, and wherein x is an integer from 2 to about 5 and y is an integer from about 3 to about 12. For example, "($C_2$-$C_9$)heterocycloalkyl" refers to a nonaromatic free radical having 3 to 10 atoms (i.e., ring atoms) that form at least one ring, wherein 2 to 9 of the ring atoms are carbon and the remaining ring atom(s) (i.e., hetero ring atom(s)) is selected from the group consisting of nitrogen, sulfur, and oxygen. As such, ($C_2$-$C_9$)heterocycloalkyl groups can be monocyclic or multicyclic. Individual rings of such multicyclic heterocycloalkyl groups can have different connectivities, e.g., fused, bridged, spiro, etc. in addition to covalent bond substitution. Exemplary ($C_2$-$C_9$)heterocycloalkyl groups include pyrrolidinyl, tetrahydrofuranyl, dihydrofuranyl, tetrahydropyranyl, pyranyl, thiopyranyl, aziridinyl, azetidinyl, oxiranyl, methylenedioxyl, chromenyl, barbituryl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, piperidinyl, thiomorpholinyl, 1,2-tetrahydrothiazin-2-yl, 1,3-tetrahydrothiazin-3-yl, tetrahydrothiadiazinyl, morpholinyl, 1,2tetrahydrodiazin-2-yl, 1,3-tetrahydrodiazin-1-yl, tetrahydroazepinyl, piperazinyl, piperizin-2onyl, piperizin-3-onyl, chromanyl, 2-pyrrolinyl, 3-pyrrolinyl, imidazolidinyl, 2-imidazolidinyl, 1,4-dioxanyl, 8-azabicyclo[3.2.1]octanyl, 3-azabicyclo[3.2.1]octanyl, 3,8diazabicyclo[3.2.1]octanyl, 2,5-diazabicyclo[2.2.1]heptanyl, 2,5-diazabicyclo[2.2.2]octanyl, octahydro-2H-pyrido[I,2a]pyrazinyl, 3-azabicyclo[4.1.0]heptanyl, 3-azabicyclo[3.1.0]hexanyl2-azaspiro[4.4]nonanyl, 7-oxa-I-aza-spiro[4.4]nonanyl, 7-azabicyclo[2.2.2]heptanyl, octahydroIH-indolyl, etc.

In general, the ($C_2$-$C_9$)heterocycloalkyl group typically is attached to the main structure via a carbon atom or a nitrogen atom. In any event, the ($C_2$-$C_9$)heterocycloalkyl group is attached to the main structure via a ring atom. Of course, other ($C_2$-$C_9$)heterocycloalkyl groups will be readily apparent to those of skill in the art given the benefit of the present disclosure.

As used herein, the terms "aryl" and "heteroaryl" refer to stable mono- or polycyclic, heterocyclic, polycyclic, and polyheterocyclic unsaturated moieties having preferably 3-14 carbon atoms, each of which may be substituted or unsubstituted. Substituents include, but are not limited to, any of the substitutents mentioned herein or for other moieties as disclosed herein, resulting in the formation of a stable compound. In certain embodiments, "aryl" refers to a mono- or bicyclic carbocyclic ring system having one or two aromatic rings including, but not limited to, phenyl, naphthyl, tetrahydronaphthyl, indanyl, indenyl, and the like. In certain embodiments, the term "heteroaryl", as used herein, refers to a cyclic aromatic radical having from five to ten ring atoms of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

It will be appreciated that aryl and heteroaryl groups can be unsubstituted or substituted, wherein substitution includes replacement of one, two, three, or more of the hydrogen atoms thereon independently with any one or more of the following moieties including, but not limited to: alkyl; heteroalkyl; aryl; heteroaryl; arylalkyl; heteroarylalkyl; alkoxy; aryloxy; heteroalkoxy; heteroaryloxy; alkylthio; arylthio; heteroalkylthio; heteroarylthio; —F; —Cl; —Br; —I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(O)$R_x$; —$CO_2(R_x)$; —CON($R_x$)$_2$; —OC(O)$R_x$; —$OCO_2R_x$; —OCON($R_x$)$_2$; —N($R_x$)$_2$; —S(O)$_2R_x$; —$NR_x$(CO)$R_x$, wherein each occurrence of $R_x$ independently includes, but is not limited to, alkyl, heteroalkyl, aryl, heteroaryl, arylalkyl, or heteroarylalkyl, wherein any of the alkyl, heteroalkyl, arylalkyl, or heteroarylalkyl substituents described herein may be substituted or unsubstituted, branched or unbranched, cyclic or acyclic, and wherein any of the aryl or heteroaryl substituents described above and herein may be substituted or unsubstituted.

As used herein, the term "($C_x$-$C_y$)aryl" refers to an aryl group consisting essentially of x to y carbon atoms in the aromatic ring(s), wherein x is an integer from about 6 to about 10 and y is an integer from about 10 to about 14. For example, "$(C_6-C_{10})$aryl" refers to an aryl group consisting essentially of 6 to 10 ring carbon atoms, e.g., phenyl and naphthyl.

As used herein, the term "$(C_x-C_y)$heteroaryl" refers to a heteroaryl group consisting essentially of x to y carbon atoms in the aromatic ring(s), wherein x is an integer from about 6 to about 10 and y is an integer from about 10 to about 20. For example, "$(C_2-C_9)$heteroaryl" refers to an aromatic free radical having 5 to 10 atoms (i.e., ring atoms) that form at least one ring, wherein 2 to 9 of the ring atoms are carbon and the remaining ring atom(s) (i.e., hetero ring atom(s)) is selected from the group consisting of nitrogen, sulfur, and oxygen. As such, $(C_2-C_9)$heteroaryl groups can be monocyclic or multicyclic. Individual rings of such multicyclic heteroaryl groups can have different connectivities, e.g., fused, etc. in addition to covalent bond substitution. Exemplary $(C_2-C_9)$heteroaryl groups include furyl, thienyl, thiazolyl, pyrazolyl, isothiazolyl, oxazolyl, isoxazolyl, pyrrolyl, triazolyl, tetrazolyl, imidazolyl, 1,3,5-oxadiazolyl, 1,2,4-oxadiazolyl, 1,2,3oxadiazolyl, 1,3,5-thiadiazolyl, 1,2,3-thiadiazolyl, 1,2,4-thiadiazolyl, pyridyl, pyrimidyl, pyrazinyl, pyridazinyl, 1,2,4-triazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl and benzoxazinyl, etc.

In general, the $(C_2-C_9)$heteroaryl group typically is attached to the main structure via a carbon atom, however, those of skill in the art will realize when certain other atoms, e.g., hetero ring atoms, can be attached to the main structure. In any event, the $(C_2-C_9)$heteroaryl group is attached to the main structure via a ring atom. Of course, other $(C_2-C_9)$heteroaryl groups will be readily apparent to those of skill in the art given the benefit of the present disclosure.

As used herein, the term, "$(C_x-C_y)$alkoxy" refers to a straight or branched chain alkyl group consisting essentially of from x to y carbon atoms that is attached through an oxygen bridge, wherein x is an integer from 1 to about 10 and y is an integer from about 2 to about 20. For example, "$(C_1-C_{20})$alkoxy" refers to a straight or branched chain alkyl group having 1-20 carbon atoms that is attached through an oxygen bridge, thus having the general formula alkyl-O—, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy. An alkoxy group may be alternatively referred to as an oxo-alkyl group.

As used herein, the term "halo" refers to fluorine, chlorine, bromine, or iodine.

As used herein, the term "amino" refers to a free radical having a nitrogen atom (i) covalently bonded to two hydrogen atoms, or alternatively (ii) covalently bonded to one hydrogen atom and one carbon radical. As such, the term amino generally refers to primary and secondary amines. In embodiments where the free radical is covalently bonded to a carbon atom, the term "amino" also includes tertiary amines. Those of skill in the art given the benefit of the present disclosure will readily be able to identify when the term "amino" is interchangeably used to refer to primary, secondary, and tertiary amines.

As used herein, the term "Grubb's catalysts: refers to a ruthenium carbene catalyst in general with first generation of the structure

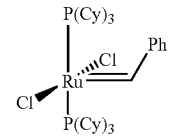

and second generation

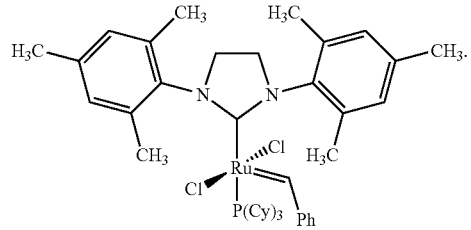

The third generation replaces the P(Cy)$_3$ with a ligand such as pyridine or 3-bromopyridine.

As used herein, the term "swelling ratio" refers to Q as defined below.

The weight of the wet hydrogel ($W_w$) and the weight of the dried hydrogel ($W_d$, after drying in a vacuum oven to remove all water) are measured at various time points and are used to calculate the swelling ratio, Q:

$$Q = \frac{W_w - W_d}{W_d} \quad (1)$$

As used herein, the term "weight average molecular weight" (or $M_w$) refers $$M_w = \frac{\sum M_i^2 N_i}{\sum M_i N_i},$$

where M is the mass of the chain and N is the number of those chains with mass M.

As used herein, the term "number average molecular weight" (or $M_w$) refers to $$M_n = \frac{\sum M_i N_i}{\sum N_i},$$

where M is the mass of the chain and N is the number of those chains with mass M.

As used herein, the term "polydispersity index" (or "PDI") refers to the ratio of the weight average molecular weight to the number average molecular weight.

BRIEF DESCRIPTION OF THE DRAWINGS

FIG. 1 shows examples of end-functionalized poly(ethylenoxide)monomers.

FIG. 2 shows an exemplary Maldi-TOF spectrum of norbornene macromonomer 2 (Matrix: 2,4-dihydroxybenzoic acid, counter ion: Na).

FIG. 3 shows an exemplary GPC trace of macromonomer 2 (left) and its intermediate (right)

FIG. 4 shows an exemplary $^1$H-NMR spectrum of the intermediate (bottom) and macromonomer 2 (top).

FIG. 5 shows exemplary GPC traces for polmers 1 (a, in DMF) 2c (b, in THF).

FIG. 6 shows exemplary Dynamic Light scattering results on 2b (a) and 3a (b).

FIG. 7 shows exemplary OxyNorbornene-Diamine Swelling Data.

FIG. 8 shows exemplary OxyNorbornene-Diacid Swelling Data.

FIG. 9 shows exemplary OxyNorbornene-Tetrahydroxy Swelling Data.

DETAILED DESCRIPTION OF THE INVENTION

The invention provides certain water-soluble and water-insoluble monomers, polymers, compositions and products comprising same, and related methods. For example, the invention provides monomers suitable for ring opening metathesis polymerization and polymers, compositions and articles comprising same, as well as related methods.

In one aspect, the invention generally relates to a substantially water-soluble monomer, or a monomer convertible to be substantially water-soluble, that is suitable for polymerization. In certain preferred embodiments, the monomer is suitable for polymerization conducted under aqueous reaction conditions, for example, wherein the polymerization is a ring-opening metathesis polymerization catalyzed by a suitable catalyst. Suitable catalysts, for example, include various Ru-based catalysts such as those selected from the first generation of Grubb's catalysts, the second generation of Grubb's catalysts and the third generation of Grubb's catalysts.

In certain preferred embodiments, the monomer is a norbornene functionalized with poly(ethylene oxide) or an oxanorbornene end-functionalized with poly(ethylene oxide), for example, the monomer is of Formula I:

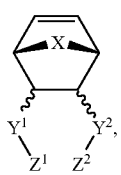

(I)

wherein
X is O, CH$_2$ or substituted CH$_2$;
Y$^1$, Y$^2$ are each independently carbonyl, (C$_1$-C$_4$) alkylene, substituted (C$_1$-C$_4$) alkylene; and
Z$^1$, Z$^2$ are each independently —OH, —OR$_z$, alkyl, —NR$_z$, substituted alkyl, aryl, substituted aryl,
  wherein
R$_z$ is an alkyl, substituted alkyl, aryl, substituted aryl, poly(ethylene oxide),
wherein Z$^1$ and Z$^2$ may together form a 5-, 6-, or 7-membered ring with the proviso that when each Y$^1$ and Y$^2$ is carbonyl, the formed ring is not a 5-membered ring with a Y$^1$ and Y$^2$ joined by a N atom.

In certain preferred embodiments, each of Y$^1$ and Y$^2$ is a carbonyl group. In certain detailed embodiments, each of Z$^1$ and Z$^2$ is independently —OR$_z$, wherein
R$_z$ is

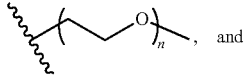, and n is an integer from 1 to 50.

In certain embodiments, X is O. In certain other embodiments, X is CH$_2$. In certain other embodiments, X is a substituted CH$_2$.

In certain embodiments, the monomer is selected from:

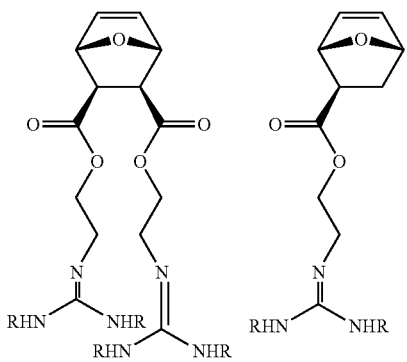

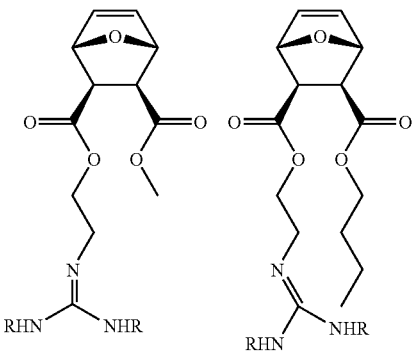

and ring-opened compounds thereof.

In certain other embodiments, the monomer is selected from:

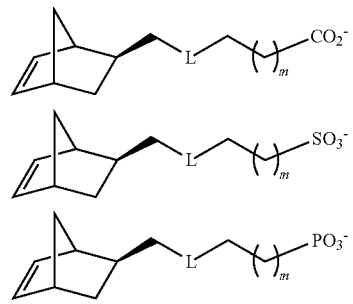

wherein m is an integer from 0 to 10; and

L is

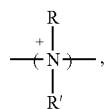

wherein R and R' is independently H, $(C_1\text{-}C_4)$ alkyl or $(CH_2CH_2O)_nR''$ where R" is H or $CH_3$ and n is an integer from 1 to 5.

In certain preferred embodiments, the monomer is selected from:

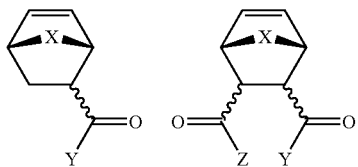

wherein Y and Z each is independently selected from

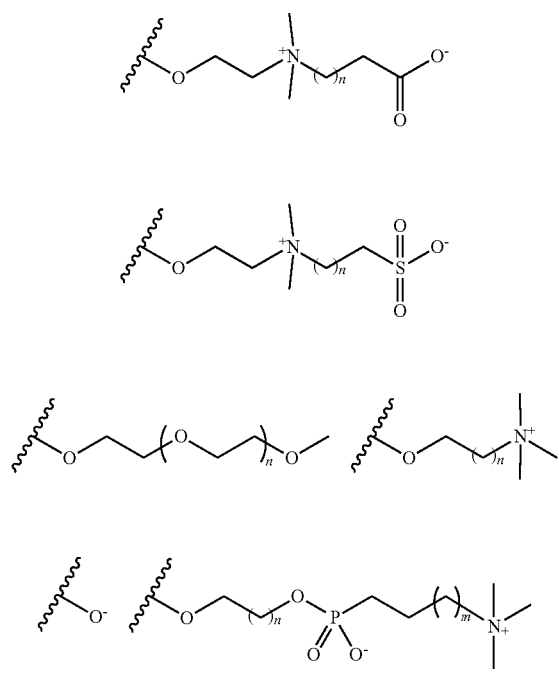

In certain preferred embodiments, the monomer is selected from:

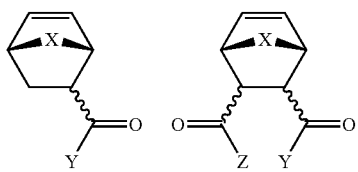

wherein Y and Z are each independently selected from

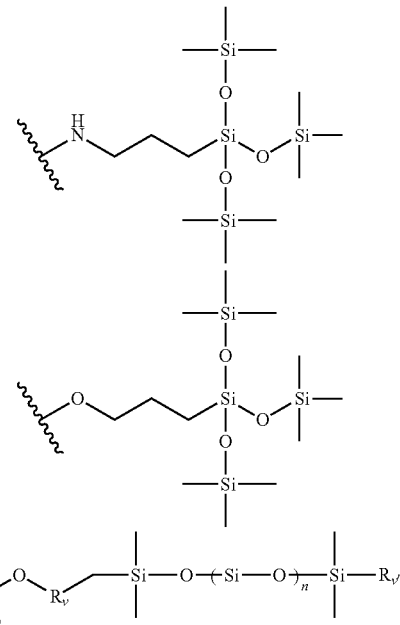

wherein n is from about 5 to about 20, $R_v$ is $-CH_2CH_2OCH_2CH_2-$ and $R_{v'}$ is $C_4H_9$

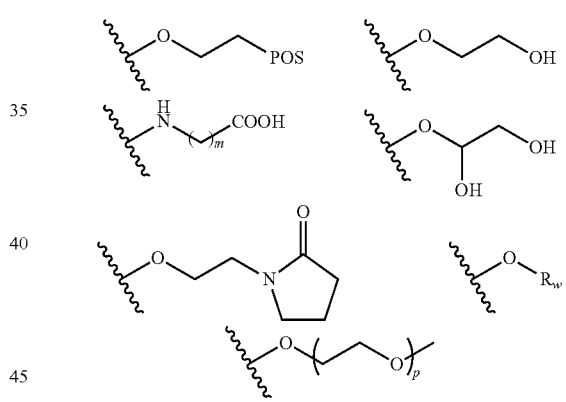

wherein POS is polyhedral oligomeric silsesquioxane; m is from about 1 to about 5; p is from about 1 to about 50; and $R_w$ is a $(C_1\text{-}C_6)$alkyl group.

In certain other preferred embodiments, the monomer is:

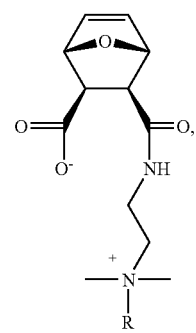

wherein R is H, $(C_1-C_4)$ alkyl or oligo(ethylene oxide) having from about 1 to about 10 ethylene oxide units, substituted alkyl group, or substituted aromatic group. In certain detailed embodiments, for example, R is selected from:

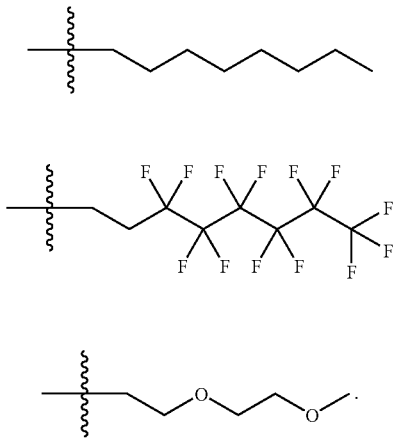

The counter anion may be a halogen anion, e.g., $Cl^-$, $Br^-$, or other anion.

In certain other preferred embodiments, the monomer is:

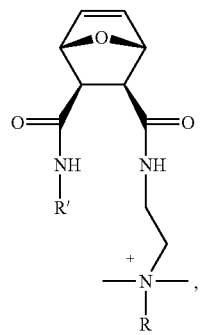

wherein R and R' are each independently H, $(C_1-C_4)$ alkyl or oligo(ethylene oxide), substituted alkyl group, aryl, or substituted aryl group. In certain detailed embodiments, for example, R and R' is independently selected from:

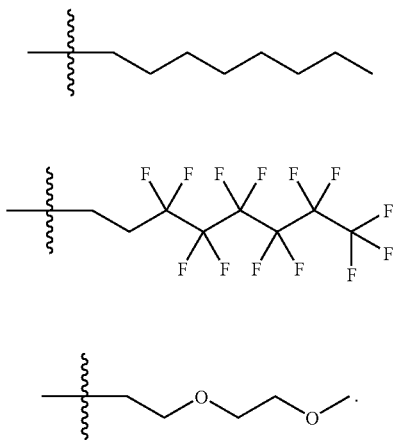

In certain other preferred embodiments, the monomer is:

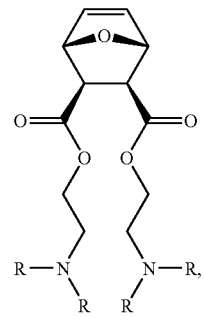

wherein each R is independently H, $(C_1-C_4)$ alkyl or oligo(ethylene oxide), substituted alkyl group, or substituted aromatic group. In one embodiment, R is methyl. In certain detailed embodiments, for example, each R is independently selected from:

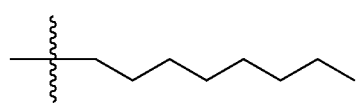

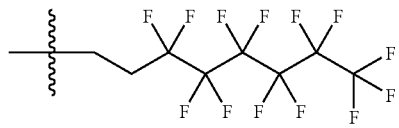

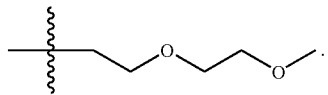

Examples of monomers also include:

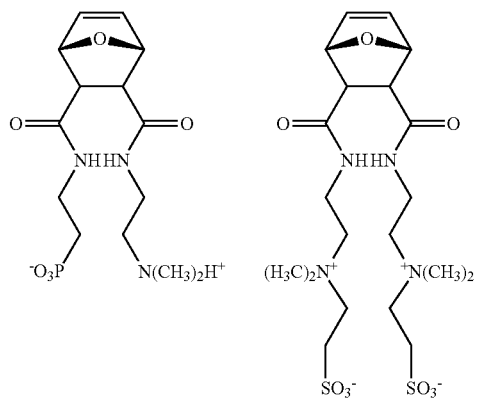

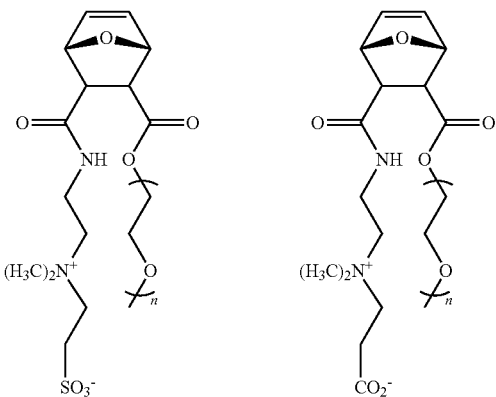

wherein n is an integer from about 1 to about 20.

In certain other preferred embodiments, the monomer is:

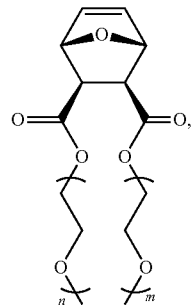

wherein n and m are each independently selected from an integer between about 1 to about 50.

In another aspect, the invention generally relates to a polymer comprising monomers of Formula Ia:

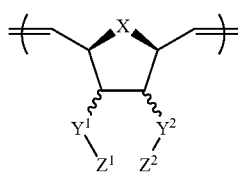

(Ia)

wherein

X is O, $CH_2$ or substituted $CH_2$;

$Y^1$, $Y^2$ are each independently carbonyl, $(C_1-C_4)$ alkylene, substituted $(C_1-C_4)$ alkylene; and $Z^1$, $Z^2$ are each independently —OH, —$OR_z$, alkyl, —$NR_z$, substituted alkyl, aryl, substituted aryl, wherein $R_z$ is an alkyl, substituted alkyl, aryl, substituted aryl, poly(ethylene oxide).

In certain preferred embodiments, each of $Y^1$ and $Y^2$ is a carbonyl group. In certain embodiments, each of $Z^1$ and $Z^2$ is independently —$OR_z$, wherein
$R_z$ is

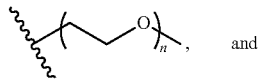

and n is an integer from about 1 to about 50.

In certain preferred embodiments, wherein X is O. In certain other preferred embodiments, X is $CH_2$. In certain other preferred embodiments, X is a substituted $CH_2$.

In certain preferred embodiments, a monomer selected from:

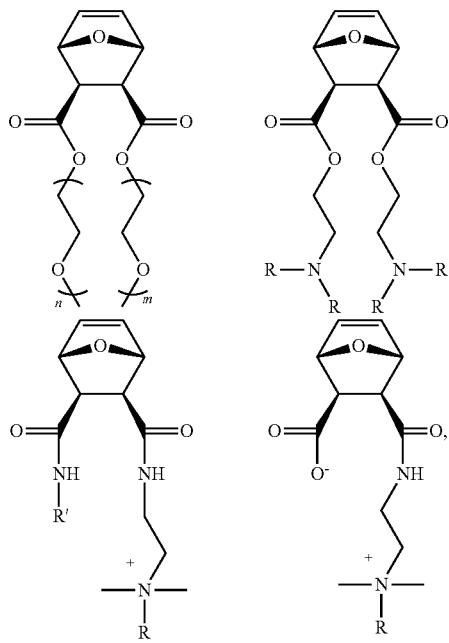

wherein each R is independently selected from:

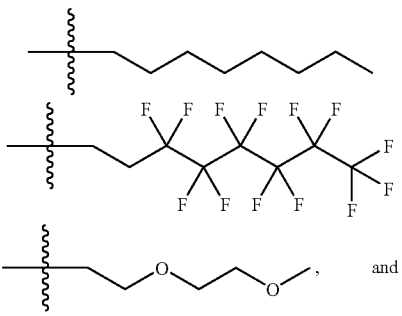

each of m and n is a number from about 1 to about 50.

In certain preferred embodiments, the polymer of the invention has one or both of: a MW from about 2,000 to about 500,000 (e.g., from about 2,000 to about 100,000, from about 10,000 to about 155,000) and having a PDI from about 1.0 to about 1.5 (e.g., from about 1.08 to about 1.40, from about 1.2 to about 1.5).

In certain preferred embodiments, the polymer of the invention is cross-linked. The cross-linked polymer may have a monomer selected from:

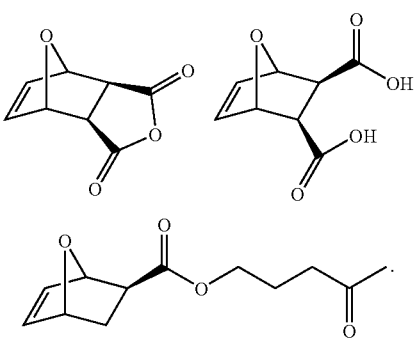

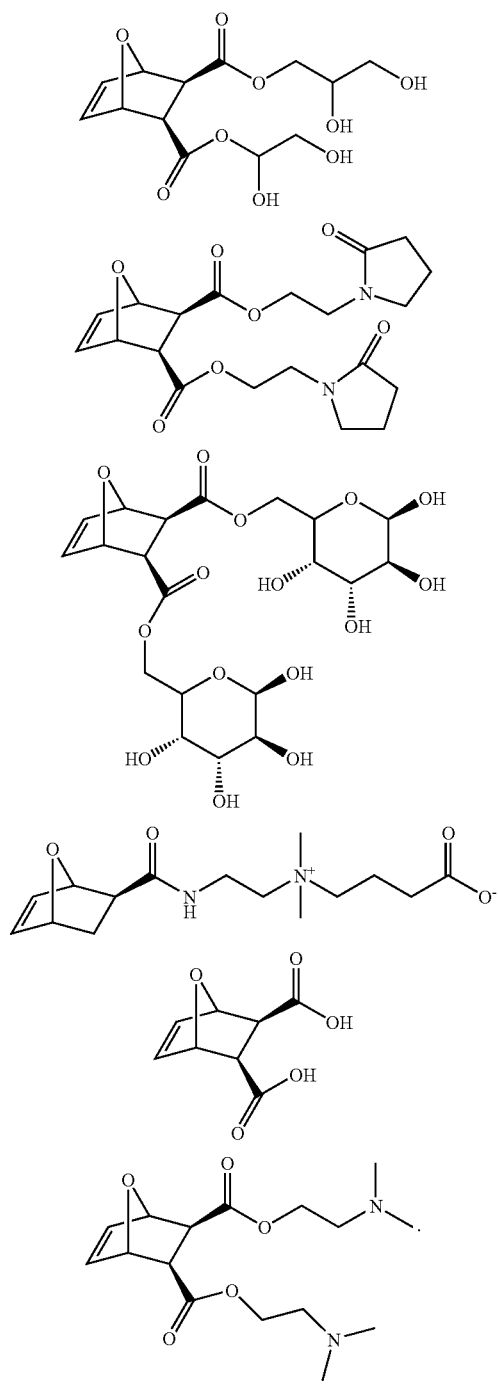

In certain preferred embodiments, the cross-linking agent is selected from: a diamine, a tri-amine, or a tetra-amine. In some embodiments, the cross-linking agent is selected from:

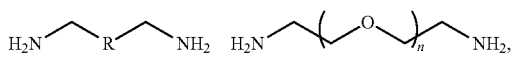

wherein R is an alkylene, substituted alkylene, aryl, substituted aryl, animo acid or peptide having from 3 to 25 amino acids; and n is any integer between 0 to 200, e.g., 5, 8, 20, 40, 50, 100, 150.

In some other embodiments, the cross-linking agent is selected from:

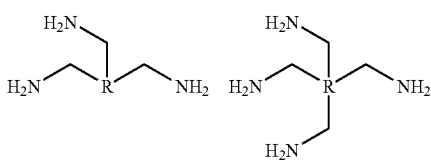

wherein R is a tri- or tetra-valent radical having anywhere from 1 to 200 carbon atoms, e.g., 5, 8, 20, 40, 50, 100, 150. For example, R is a tri- or tetra-valent radical of alkyl, substituted alkyl, aryl, or substituted aryl, or a peptide having from 3 to 25 amino acids.

In certain preferred embodiments, the cross-linking agent is a dithiol selected from:

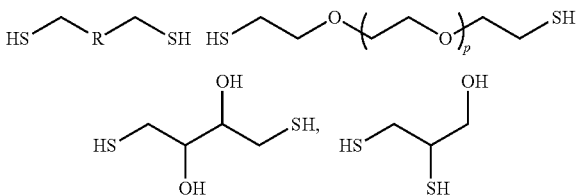

wherein R is an alkylene, substituted alkylene, aryl, or substituted aryl, amino acid and peptide having 3 to 25 amino acids; p is any integer between 0 to 200, e.g., 5, 8, 20, 40, 50, 100, 150.

In certain preferred embodiments, the cross-linking agent is selected from:

In certain preferred embodiments, the polymer is a co-polymer, for example, a statistical co-polymer or a gradient co-polymer.

In certain preferred embodiments, the polymer includes two or more blocks of different monomers of Formula Ia. In certain other preferred embodiments, the polymer has monomers of Formula Ia and one or more blocks of other monomers.

In certain embodiments, the co-polymer comprises co-monomer selected from:

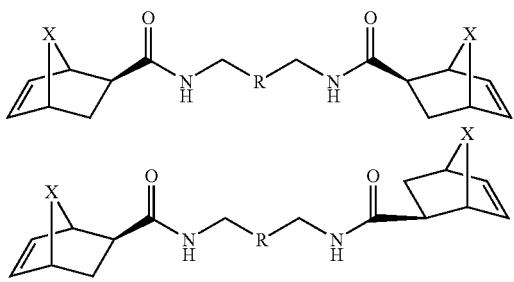

wherein
X is O or —CH$_2$— or substituted —CH$_2$—;
R is —(CH$_2$)$_m$—, —(CH$_2$CH$_2$O)$_n$—, or a peptide of 3 to 25 amino acids:
m is from 0 to 30, and
n is from 1 to 3000.

In certain preferred embodiments, the cross-linking agent is selected from:

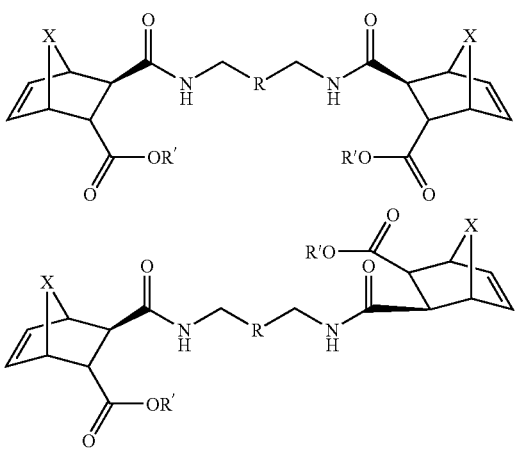

wherein
X is O or —CH$_2$— or substituted —CH$_2$—;
R is —(CH$_2$)$_m$—, —(CH$_2$CH$_2$O)$_n$—, or a peptide of 3 to 25 amino acids;
R' is an alkyl, aryl, —CH$_2$CH$_2$NCH$_3$, —(CH$_2$CH$_2$O)$_n$CH$_3$;
m is from 0 to 30, and
n is from 1 to 3000.

In certain preferred embodiments, the cross-linking agent is selected from:

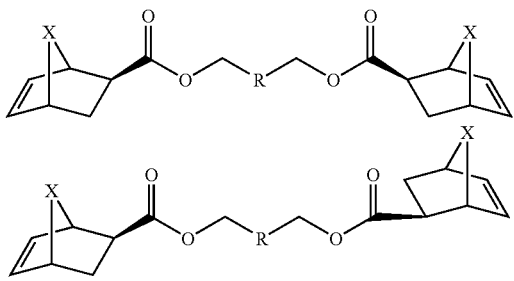

X is O or —CH$_2$— or substituted —CH$_2$—;
R is —(CH$_2$)$_m$—, —(CH$_2$CH$_2$O)$_n$—, or a peptide of 3 to 25 amino acids;
m is from 0 to 30, and
n is from 1 to 3000.

In certain preferred embodiments, the cross-linking agent is selected from:

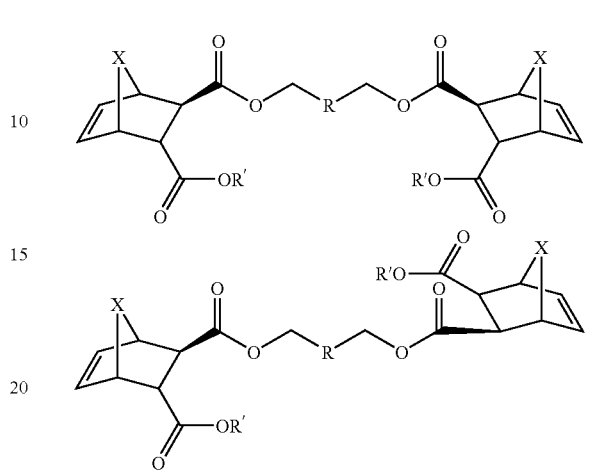

X is O or —CH$_2$— or substituted —CH$_2$—;
R is —(CH$_2$)$_m$—, —(CH$_2$CH$_2$O)$_n$—, or a peptide of 3 to 25 amino acids;
R' is an alkyl, aryl, —CH$_2$CH$_2$NCH$_3$, —(CH$_2$CH$_2$O)$_n$CH$_3$;
m is from 0 to 30, and
n is from 1 to 3000.

In certain preferred embodiments, the cross-linking agent comprises one selected from:

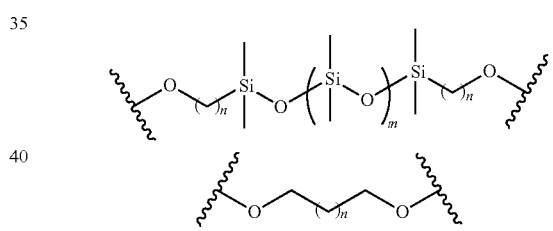

wherein
m each is independently selected from an integer from 5 to 25; and
n each is independently selected from an integer from 0 to 3.

Cross-linking may be conducted with one, two, or more cross-linking agents.

In certain embodiments, the polymer has a swelling ratio of from about 0.1 to about 3,000. In certain preferred embodiments, the polymer has a swelling ratio of from about 0.5 to about 700, about 1 to about 150, or about 2 to about 70.

In yet another aspect, the invention generally relates to a method for producing a polymer, comprising contacting water-soluble monomers with one or more catalysts under conditions that allow polymerization of the monomers to obtain water-soluble polymers.

In certain preferred embodiments, the polymerization is by way of a ring-opening metathesis polymerization. In certain detailed embodiments, the monomer(s) and Ru-based catalyst are dissolved in a suitable solvent (like dichloromethane) and subject to three freeze-thaw cycles. For example, the catalyst is added in one shot to the vigorously stirring monomer solution at room temperature under argon. After 30 minutes, the polymerization is terminated with an excess of ethylvinyl ether (e.g., 1 mL, 754 mg, 10.5 mmol). Conditions vary depending on monomer and cross-linker.

The invention also encompasses compositions and articles of manufacture comprising the monomer or polymer of the invention. For example, an article may be made with cross-linked polymer of the invention. The swelling ratio, for example, may be from about 30 to about 150, from about 30 to about 100, from about 30 to about 50. In certain other embodiments, the polymer has a swelling ratio of less than about 1.0, less than about 0.5, less than about 0.3, or less than about 0.2.

An example of such articles having polymers of the invention is a contact lens or material used thereof. Other examples include molded parts with desired water content and powders for rapid swelling.

Additional exemplary monomers include monomers selected from:

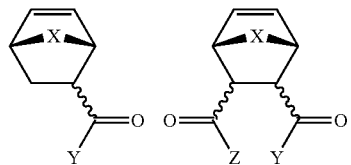

wherein
X is O or —CH$_2$— or substituted —CH$_2$—;
Y, Z are each independently selected from

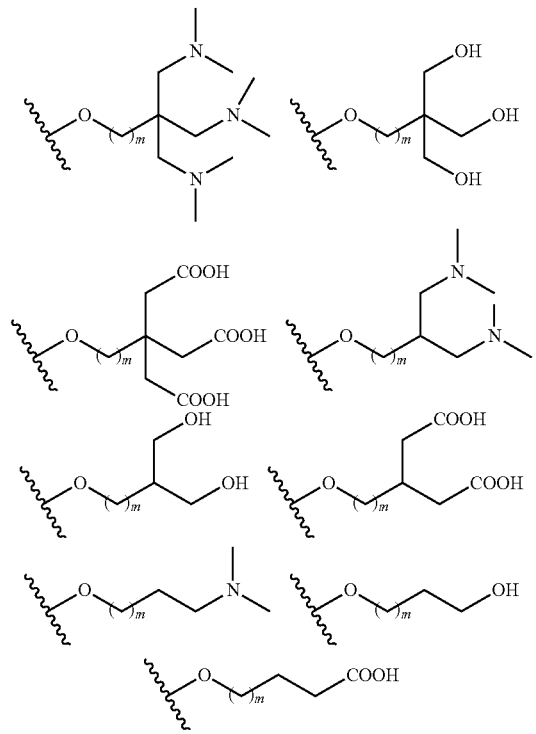

wherein each m is independently 0 or 1.

Some examples of substituents of the above-described moieties of monomers and polymers of the invention include, but are not limited to: $(C_x$-$C_y)$alkyls, wherein x is an integer from 1 to about 10 and y is an integer from about 2 to about 20; $(C_x$-$C_y)$cycloalkyl, wherein x is an integer from 1 to about 10 and y is an integer from about 2 to about 20; $(C_x$-$C_y)$heterocycloalkyl, wherein x is an integer from 2 to about 5 and y is an integer from about 3 to about 12; $(C_2$-$C_9)$heterocycloalkyl; $(C_x$-$C_y)$aryl, wherein x is an integer from 6 to about 10 and y is an integer from about 10 to about 14; $(C_x$-$C_y)$heteroaryl, wherein x is an integer from 6 to about 10 and y is an integer from about 10 to about 20; $(C_x$-$C_y)$alkoxy, wherein x is an integer from 1 to about 10 and y is an integer from about 2 to about 20.

Examples of substituents of the above-described moieties of monomers and polymers of the invention also include, but are not limited to: halogen; amino; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, arylalkyl, or heteroarylalkyl, wherein any of the aliphatic, heteroaliphatic, arylalkyl, or heteroarylalkyl substituents described above and herein may be substituted or unsubstituted, branched or unbranched, cyclic or acyclic, and wherein any of the aryl or heteroaryl substituents described herein may be substituted or unsubstituted. Additional examples of generally applicable substituents are illustrated by the specific embodiments shown in the Examples that are described herein.

Isotopically-labeled compounds are within the scope of the present disclosure. As used herein, an "isotopically-labeled compound" refers to a presently disclosed compound including pharmaceutical salts, esters and prodrugs thereof, in which one or more atoms are replaced by an atom having an atomic mass or mass number different from the atomic mass or mass number usually found in nature. Examples of isotopes that can be incorporated into compounds presently disclosed include isotopes of hydrogen, carbon, nitrogen, oxygen, phosphorous, fluorine and chlorine, such as $^2$H (deuterium or "D"), $^3$H, $^{13}$C, $^{15}$N, $^{18}$O, $^{17}$O, $^{31}$P, $^{32}$P, $^{35}$S, $^{18}$F and $^{36}$Cl, respectively. By isotopically-labeling the presently disclosed compounds, the compounds may be useful, for example, in drug and/or substrate tissue distribution assays.

Incorporation by Reference

References and citations to other documents, such as patents, patent applications, patent publications, journals, books, papers, web contents, have been made throughout this disclosure. All such documents are hereby incorporated herein by reference in their entirety for all purposes.

Equivalents

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. The following examples contain important additional information, exemplification and guidance which can be adapted to the practice of this invention in its various embodiments and equivalents thereof.

EXAMPLES

The following non-limiting examples and data illustrate various aspects and features relating to the monomeric components, polymers and/or methods of the present invention, including the preparation of water-soluble and water-insoluble polymerization products, as are available through the synthetic methodologies described herein. In comparison with the prior art, the present monomers, polymers, articles and/or methods provide results and data which are surprising and unexpected. While the utility of this invention is illustrated through the use of several polymers, monomers and substituents thereof, it will be understood by those skilled in the art that comparable results are obtainable with various other polymers, monomers and/or monomeric substituents, as are commensurate with the scope of this invention.

Materials: 5-Norbornene-2,3-dicarboxylic anhydride (endo) (99%), Triphenylphosphine ($Ph_3P$) (99%), (Diisopropylazodicarboxylate (DIAD) (94%), 3-Bromopyridine (94%), 4-(Dimethylamino)pyridine (DMAP) (94%), Furan (99%) and Maleic anhydride (95%) were purchased from Sigma-Aldrich and used without further purification. N,N'-Dicyclohexylcarbodiimide (DCC) (95%) and mono-methyl-ether poly(ethylene oxide) (PEO—OH) [$M_n$=1100, PDI=1.04; $M_n$=1900 PDI=1.05] were purchased from Fluka. Prior to use PEO—OH was heated at 120° C. for 3 hours under nitrogen atmosphere to remove excess water. Grubbs' Catalyst (G3) used in the polymerization was synthesized according to a published procedure from second generation Grubbs' Catalyst (G2), which was purchased from Sigma Aldrich and used as received. (Love, et al., *Angew Chem Int Ed* 2002, 41, 4035.) Spectrophotometric grade pentane (>99%) was purchased from Sigma. Tetrahydrofuran (THF), from Sigma, was distilled over sodium and benzophenone under $N_2$ before use.

Instrumentation: $^1H$ NMR and $^{13}C$ NMR spectra were recorded on a 300 MHz Bruker Spectrospin 300. Gel permeation chromatography (GPC) in DMF and THF was performed using a Polymer Laboratories PL-GPC50 instrument with two to three 5 μm mixed-D columns, a 5 μm guard column, and a Knauer RI detector. The apparatus was calibrated against polystyrene standards, with toluene as the flow marker. Static and dynamic light scattering experiments were performed at room temperature using an ALV unit equipped with an ALV/SP-125 precision goniometer (ALV-Laser Vertriebsgessellschaft m.b.h., Langen, Germany), an Innova 70 argon laser (λ=514.5 nm, max. power 3 W, CoherentInc.) operated at 300 mW, and a photomultiplier detector (Thorn EMI Electron Tubes). Signal from the detector was processed by an ALV5000 Multiple Tau Digital Correlator board and associated software.

To obtain water-soluble polymers with poly(ethylene oxide) side chains, the macromonomer approach was chosen. The PEO macromonomers 1-3 depicted in FIG. 1 were obtained by attaching PEO to norbornene derivatives.

Scheme 1. Synthesis of norbornene macromonomer 1

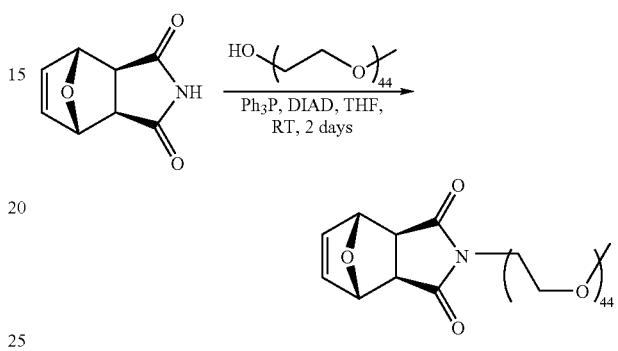

First investigated was the synthesis and polymerization of monomer 1 (Scheme 1). This monomer was polymerized molecular weights between 20 000-50 000 g/mol, however, the polydispersities obtained were always broad, typically around 1.6, and multi-modal similar to literature reports. (Biagini, et al. *J Polymer Sci Part A: Polymer Chem* 2007, 45, 3178.) With the future prospect of generating block copolymers in mind, this monomer was abandoned. Monomers 2 and 3 were designed to see if a compatible monomer could be obtained and, at the same time, learn which structural element of monomer 1 was leading to broad PDI. Because the number of repeat units of PEO in monomer 1 was 44, PEO was chosen with 25 repeat units for monomers 2 and 3, to make the total degree of polymerization (DP) of PEO similar between all three monomers (44 vs. 50). The synthesis of 2 is shown in Scheme 2.

Scheme 2. Synthesis of norbornene macromonomer 2

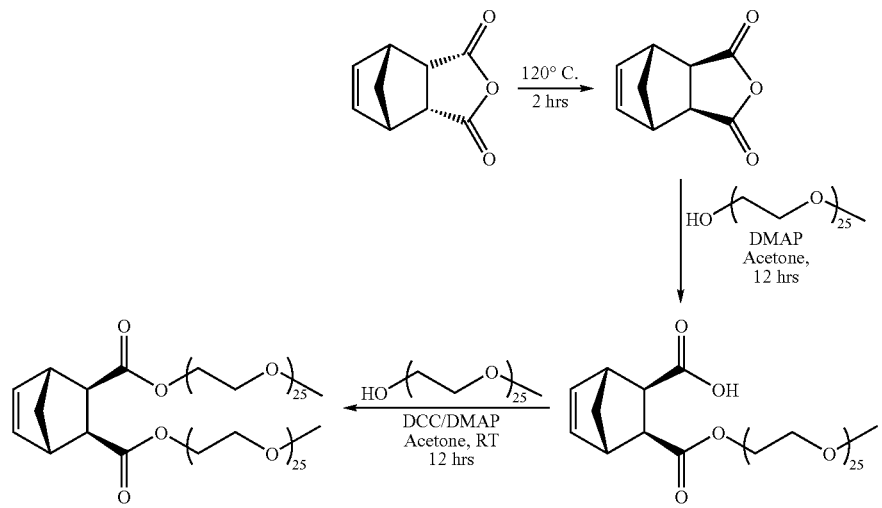

In the first step, the commercially available endo-5-norbornene-2,3-dicarboxylic anhydride isomer was converted into the exo isomer. This was necessary for two reasons: first, endo isomers react much slower than exo isomers, and secondly due to steric hindrance the PEO chains are more difficult to attach to the endo isomer than to the exo isomer. The endo isomer was heated to 210° C. under nitrogen for 2 hours. Recrystallizations from either toluene or benzene afforded the exo-isomer, but in only 14% yield. While the yield of this reaction is low, the commercially available starting material is inexpensive which more than compensates for the poor yield. Attachment of PEO followed in a two step process as shown in Scheme 2. First, the anhydride was ring opened by PEO with dimethylaminopyridine (DMAP) as a catalyst (90% yield). Then, ester coupling conditions were used to attach the second arm of PEO to the remaining free carboxylic acid in 65% yield. This design allows easy attachment of various PEO chain lengths, or other functionalities. Also, asymmetrical monomers with different functional groups can be synthesized as shown via the intermediate in Scheme 2 (the mono PEO, mono acid monomer). FIG. 3 shows the GPC trace of the intermediate with one PEO side chain, as well as macromonomer 2. As can be seen from the GPC trace, the intermediate (eluting at longer retention times than macromonomer 2) is monomodal. Residual PEO—OH overlaps with the functionalized intermediate. When attaching the second PEO arm, the macromonomer 2 obtained shows a slight bimodality (shoulder at the low molecular weight flank) due to a few percent residual PEO—OH. The proton NMR for the intermediate and macromonomer 2 are shown in FIG. 4. The peaks at 3.0 and 3.2 ppm in the intermediate (bottom) fuse into on peak at 3.1 ppm for the macromonomer (top) due to the increase in symmetry of the molecule. This is a clear indication that the macromonomer is quantitatively functionalized with two PEO chains per repeat unit. The residual PEO—OH was removed after polymerization of the macromonomers by precipitation.

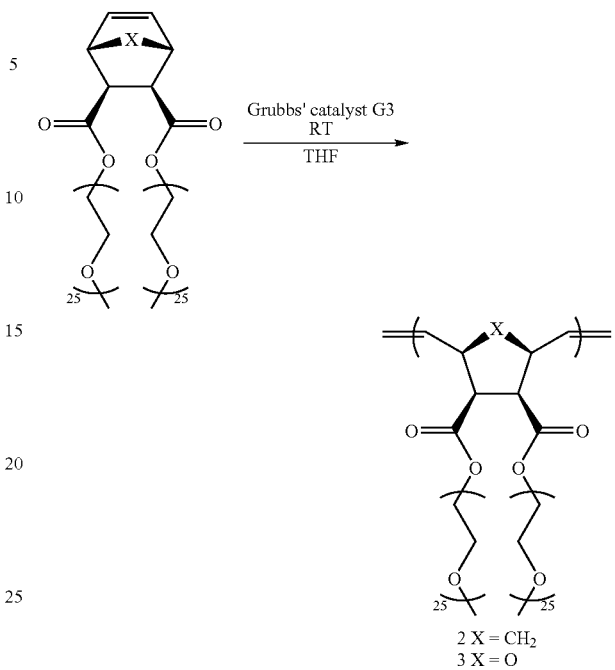

Typically, the degassed monomer solution was added to a solution of the Grubbs' Catalyst. The reverse addition was also performed with no adverse affects on the polymerization.

GPC traces of the polymers are shown in FIG. 5. In FIG. 5a, the GPC trace of polymer 1, with a PDI of 1.6 and a molecular weight of 50,000 g/mol, is shown. FIG. 5b shows a GPC trace that is representative for polymers 2, again $M_n$ is 50,000 g/mol, but the PDI is much lower (1.04). GPC traces of

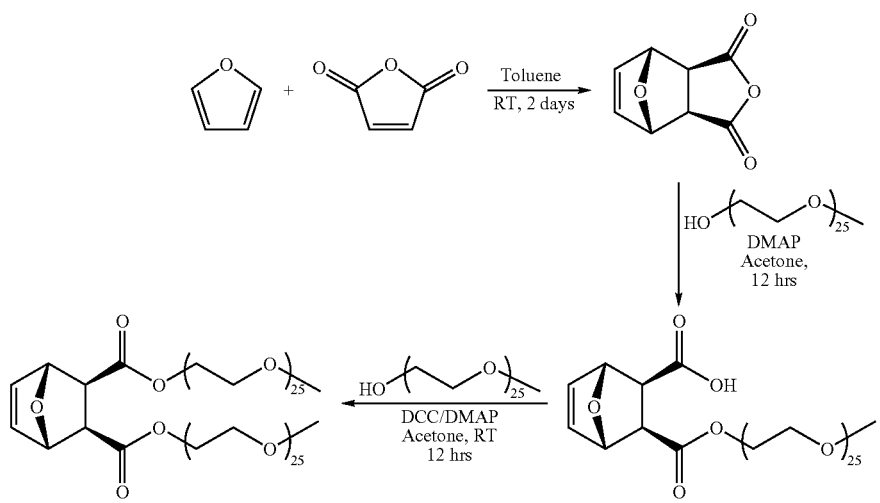

The synthesis of macromonomer 3 is shown in Scheme 3 with details below. The GPC and NMR results obtained were similar to the ones shown in FIG. 3 and FIG. 4. Both macromonomers 2 and 3 easily polymerized, at concentrations above 0.037 mol/L, to near quantitative yield in 7-40 minutes depending on the desired molecular weight (Scheme 4).

polymers 3 look comparable. As can be seen, the line profile is perfectly symmetrical with no observable high or low molecular weight shoulders, which occur frequently when macromonomers are polymerized. The facile ability of monomers 2 and 3 to polymerize with polydispersities below 1.17 suggests that the imide in monomer 1 plays a central role in its inability to yield molecules with narrow polydispersity. However, other functionalized versions of this imide monomer are well-known to yield high molecular weight polymers with narrow polydispersity. (Grubbs, D. J *Tetrahedron* 2004, 60, 7117.) Since Breitenkamp et al. (Breitenkamp, et al., *J Polymer Sci Part A: Polymer Chem* 2005, 43, 5715) and Biagini et al.[22] (Biagini, et al., *J Polymer Sci Part A: Polymer Chem* 2007, 45, 3178) observed similar problems when copolymerizing their PEO functionalized imide monomer (however using first generation Grubbs' catalyst), the difficulties seem to be caused by the combination of PEO with the imide functionality.

The analytical data for the polymerizations of macromonomers 2 and 3 is summarized in Table 1. Conversions are quantitative, and yields refer to purified polymer. The number average molecular weights obtained from gel permeation chromatography (GPC) in THF (calibrated with polystyrene) were all approximately half the targeted ones. This disparity can be attributed to different hydrodynamic volumes of these polymers compared to the calibration standard. Additionally, polymers from monomers 1-3 are all comb-like in architecture. It has been shown GPC underestimates the molecular weights of comb-like polymers. (Nakamura, et al, *Macromolecules* 2000, 33, 8323; Sun, et al., *Macromolecules* 2004, 4304.) To confirm that this is the reason for this discrepancy, GPC-MALLS was run in DMF on polymer 2c. With a literature value for the refractive index increment dn/dc of 0.05 ml/g the value obtained was 40 000 g/mol, which is in good agreement with the 46 000 g/mol calculated.

Water solubility of a polymeric material is best demonstrated by showing that the sample exists as single chains in dilute solution. Often the empirical demonstration that a certain mass of solid is dissolved in water to give a clear solution is misleading since the chains can aggregate into 10-300 nm structures which are clear to the eye. Therefore, light scattering methods were used to demonstrate water solubility of these polymers. The results from light scattering are summarized in Table 2, and FIG. 6 shows two representative field correlation functions collected from polymers 2b and 3a, respectively, along with the corresponding relaxation time distributions. As can be seen from this data, sample 2b with the norbornene backbone is monomodal (with negligible aggregation), whereas polymer 3a with the oxanorbornene backbone is aggregated (small aggregates of 3-4 molecules according to static light scattering). For a chemist, this finding is counterintuitive: the more polar oxanorbornene would be expected to bestow better water solublity to the molecule. When looking at the second virial coefficients $A_2$ for these samples, it is found that both are small and negative, indicating that water is a poor solvent or at best a theta solvent for these polymers. The value for 3a is more negative than that for 2b, thus aggregation occurs to replace the unfavorable solvent-polymer contacts by enthalpically favouralbe polymer-polymer contacts. (Huglin, M. B. Light Scattering from Polymer Solutions, Academic Press, London 1972; Literature value for pure polyethylene oxide in water: $2 \cdot 10^{-5}$ mol cm$^3$ g$^{-2}$, from: Brandrup, et al. Polymer Handbook, 4$^{th}$ edition, Wiley-Interscience, Hoboken, N.J. 1999.)

The weight average molecular weights $M_w$ determined from static light scattering confirm that 2b is molecularly dissolved, while 3a is aggregated: the value for 2b is 56,600 g/mol. Comparing this value with the calculated number average molecular weight $M_n$ for this molecule which is 46,000 g/mol along with the measured polydispersity index of 1.17 gives a $M_{w,calculated}$ around 52,000 g/mol, in good agreement with the accuracy of the methods used. This confirms that GPC underestimated the molecular weight of this sample by a factor of 2.3. For sample 3a, $M_w$ found by static light scattering is larger by a factor of three than the expected value, which is in line with the aggregation seen in dynamic light scattering.

Provided here is a new and efficient method to obtain poly(ethyleneoxide) macromonomers with a norbornene and oxanorbornene end group that polymerize by ROMP. By this approach, good control over the molecular weight and the molecular weight distribution, as well as high conversions, are obtained. The versatility of the monomer synthesis and relative ease of polymerization affords the ability to synthesize a variety of water soluble copolymers which will be reported in due course. In addition to the monomers reported here (two PEG chains per norbornene monomer), this synthetic approach has the added advantage that asymmetric monomers can be produced. It is demonstrated by light scattering techniques that the norbornene-based polymers 2 are indeed dissolved at the molecular level, while the samples with an oxanorbornene backbone, 3, form small aggregates. (Rühe, et al., *Adv Polymer Sci* 2004, 165, 79; Lienkamp, et al., *Macromolecules* 2007, 40, 2486.)

In addition to the monomers reported here (two PEG chains per norbornene monomer), this synthetic approach has the added advantage that asymmetric monomers can be produced. It has been demonstrated by light scattering techniques that the norbornene-based polymers 2 are indeed dissolved at the molecular level, while the samples with an oxanorbornene backbone, 3, form small aggregates. It has been found previously that the backbone can impact the aggregation behavior of water soluble cylindrical polymer brushes. A similar phenomena is found here for the norbornene and oxanorbornene based polymers. Due to their solubility, high functional group density, and low cost of the starting materials, polymers 2a-c are promising candidates for aqueous phase applications.

Example 1

Synthesis of Monomer 1. (1) The maleimide precursor Z (Scheme 1) was synthesized after literature procedures (Kwart, et al., *J Am Chem Soc* 1952, 74, 3094) with an isolated yield of 85%. $^1$H NMR (300 MHz, CDCl$_3$) δ 11.15 (s, 1H), 6.52 (s, 2H), 5.10 (s, 2H), 2.84 (s, 2H). $^{13}$C NMR (300 MHz, DMSO-d$_6$) δ 178.35, 136.93, 80.78, 48.89. (2) A 500 mL round bottom flask, cooled in an ice bath, was charged with a solution mixture of Z (3.3 g, 20 mmol), Ph$_3$P (5.3 g, 20 mmol) and PEO—OH ($M_n$~2000 g/mol; 13.3 g, 6.70 mmol) in dry THF (300 mL), followed by the drop-wise addition of DIAD (3.9 mL, 20 mmol). The ice bath was removed after the DIAD addition was completed and the reaction mixture was allowed to stir at room temperature for two days. Solvent was then removed under reduced pressure and the crude product was purified by column chromatography (SiO$_2$), eluting first with ethyl acetate followed by 85:15 dichloromethane:methanol. Solvent removal under reduced pressure, afforded a white solid product in 70% yield.

$^1$H NMR (300 MHz, DMSO-d$_6$) δ 6.05 (s, 2H), 5.11 (s, 2H), 3.50 (m, 182H), 2.93 (s, 2H). $^{13}$C NMR spectra were collected but due to the size of the PEO chains, only signals from the carbons on the PEO side chains were visible.

Example 2

Synthesis of Monomer 2: (1) Conversion of the endo to the exo isomer was adapted from previous literature procedures. (Canonne, et al., *J Org Chem* 1982, 47, 3953) 100 g (0.60 mol) of 5-Norbornene-2,3-dicarboxylic anhydride (endo)

was placed in a 250 mL round bottom flask and heated at 210° C. under nitrogen for 2 hours. The flask was cooled to 120° C. after which toluene (100 mL) was added. This solution was allowed to cool to room temperature. The resulting mixture was filtered and the residue was recrystallized 4 times from toluene to give white crystals of 5-norbornene-2,3-dicarboxylic anhydride (exo), (14 g, 0.14 mol, 14% yield, mp=143° C.). $^1$H NMR (300 MHz, CDCl$_3$) δ 1.44 (d, J=1.2 Hz, 1H), 1.66 (d, J=1.2 Hz, 1H), 3.01 (s, 2H), 3.47 (s, 2H), 6.34 (d, J=10.2 Hz, 2H). $^{13}$C NMR (300 MHz, CDCl$_3$) δ 171.61, 137.95, 48.77, 46.87, 44.11. (2) 6.2 g (5.7 mmol) of PEO—OH (M$_n$=1100 g/mol) was placed in a 100 mL round bottom flask. The solid was heated for 3 hours at 120° C. After cooling to room temperature, 10 mL of acetone was added followed by 0.5 g (3 mmol) of exo 5-norbornene-2,3-dicarboxylic anhydride. 0.037 g DMAP (10 mol %, 0.3 mmol) was added and the reaction was stirred for 12 hours. 1.0 g (4.8 mmol) of DCC were then added and the reaction was stirred for 12 hours. The mixture was then filtered, and the monomer was purified by three precipitations from diethyl ether. Yield=65%. $^1$H NMR (300 MHz, CDCl$_3$): δ 1.50 (d, J=1.2 Hz, 1H), 1.66 (d, J=1.2 Hz, 1H), 2.65 (s, 2H), 3.10 (s, 2H), 3.38 (s, 3H), 3.65 (s, 4H), 3.88 (m, 2H), 4.11 (m, 2H), 4.27 (m, 2H), 6.21 (s, 2H). $^{13}$C NMR spectra were collected but due to the size of the PEO chains, only signals from the carbons on the PEO side chains were visible. The structure of the macromonomer was further confirmed by Maldi-TOF MS (FIG. 2). The peak labelled at 2525 Da was chosen as an illustration. This value corresponds to two PEO chains with a repeat unit of 26 (n) for each chain, the end group molecular weights are 212 (one norbornene anhydride and two methyl fragments), and one sodium counter ion. If we sum these values, (44·26)·2+212+23, we obtain a m/z of 2523 Da.

Example 3

Synthesis of Monomer 3: (1) A 250 mL round bottom flask was charged with a solution mixture of furan (10 g, 146 mmol), maleic anhydride (13 g, 100 mmol) and 100 mL toluene. This solution was left for two days at room temperature after which the precipitated product, exo-7-oxabicyclo[2.2.1]hept-5-ene-2,3-dicarboxylic anhydride, was filtered and washed with cold toluene. Yield=90%. $^1$H NMR (300 MHz, DMSO-d$_6$) δ 6.58 (s, 2H), 5.35 (s, 2H), 3.32 (s, 2H). $^{13}$C NMR (300 MHz, DMSO-d$_6$) δ 172.01, 137.31, 82.10, 49.53. (2) 5 g (2.63 mmol) of PEO—OH (M$_n$=1100 g/mol) was placed in a 100 mL round bottom flask. This solid was heated for 3 hours at 120° C. After cooling to room temperature, 10 mL of acetone was added followed by 0.5 g (3 mmol) of 7-oxanorbornene 0.037 g DMAP (10 mol %, 0.3 mmol) was added and the reaction was stirrd for 12 hours. 1 g (4.8 mmol) of DCC was then added and the reaction was stirred for 12 hours. The mixture was then filtered, and the monomer was purified by three precipitations from diethyl ether. Yield=55%. $^1$H NMR (300 MHz, CDCl$_3$): δ 2.82 (s, 2H), 3.40 (s, 3H), 3.65 (s, 4H), 3.90 (m, 2H), 4.13 (m, 2H), 4.27 (m, 2H), 5.25 (s, 2H), 6.44 (s, 2H). $^{13}$C NMR spectra were collected but due to the size of the PEO chains, only signals from the carbons on the PEO side chains were visible.

Example 4

Polymerization of Monomer 1: In a representative experiment, 5 mL of THF was degassed by three freeze-pump-thaw cyles. 200 mg (0.09 mmol) of monomer 1 and 4 mg (2.2 µmol) Grubbs' catalyst were placed in two reaction vessels and evacuated for five minutes. 2 mL of THF was added to the monomer flask and 1 mL of THF to the catalyst. The solutions were further degassed by an additional freeze-pump-thaw cycle. After reaching room temperature, the solution of 1 was added to the G3 solution and the reaction stirred vigorously for 20 mins. The polymerization was terminated by the addition of 2 mL of ethyl vinyl ether. The polymer was then precipitated from diethyl ether to yield a white powder. Yield=100%.

Example 5

Polymerization of Monomer 2: In a typical experiment, 5 mL of THF was degassed by three freeze-pump-thaw cycles. 200 mg (55 µmol) of 2 and 2 mg (2.2 µmol) third-generation Grubbs' catalyst (G3) were then placed in two reaction vessels and evacuated for five minutes. 1 mL of THF was added to the monomer flask and 0.5 mL of THF to the catalyst. The solutions were further degassed by an additional freeze-pump-thaw cycle. After reaching room temperature, the solution of 2 was added to the G3 solution and the reaction was stirred vigorously for 20 minutes. The polymerization was terminated by the addition of 2 mL of ethyl vinyl ether. The polymer was then precipitated from diethyl ether to yield an off-white powder.

Yield=85%. $^1$H NMR: (300 MHz, CDCl$_3$): δ 1.21 (bs, 1H), 1.73 (bs, 1H), 2.06 (bs, 2H), 2.84 (bs, 2H), 3.39 (s, 3H), 3.65 (bs, 4H), 3.89 (m, 1H), 4.14 (bs, 4H), 5.20 (bs, 1H), 5.41 (bs, 1H).

Example 6

Polymerization of Monomer 3: In a representative experiment, 5 mL of THF was degassed by three freeze-pump-thaw cycles. 200 mg (55 µmol) of 3 and 2 mg (2.2 µmol) third-generation Grubbs' catalyst (G3) were then placed in two reaction vessels and evacuated for five minutes. 1 mL of THF was added to the monomer flask and 0.5 mL of THF to the catalyst. The solutions were further degassed by an additional freeze-pump-thaw cycle. After reaching room temperature, the solution of 3 was added to the G3 solution and the reaction was stirred vigorously for 20 minutes. The polymerization was terminated by the addition of 2 mL of ethyl vinyl ether. The polymer was then precipitated from diethyl ether to yield a white powder. Yield=90%. $^1$H NMR (300 MHz, CDCl$_3$): δ 3.09 (bs, 2H), 3.40 (s, 3H), 3.65 (bs, 4H), 3.89 (m, 2H), 4.20 (bs, 4H), 4.62 (bs, 2H), 5.84 (bs, 2H).

TABLE 1

Polymerization results for monomers 1-3: Number average molecular weights M$_n$ and polydispersity indices were measured by GPC (THF/polystyrene calibration), yields were determined gravimetrically from amount of purified polymer obtained, DP was calculated from the monomer:initiator feed ratio.

| Sample | [M] × 10$^{-5}$ mol/L | [I] × 10$^{-6}$ mol/L | DP | M$_{n, calculated}$ g/mol | M$_{n, GPC}$ g/mol | Yield % | PDI |
|---|---|---|---|---|---|---|---|
| 1a | 5.2 | 2.9 | 18 | 34,000 | 15,000 | 85 | 1.60 |
| 2a | 2.7 | 2.8 | 10 | 35,000 | 14,000 | 90 | 1.15 |

TABLE 1-continued

Polymerization results for monomers 1-3: Number average molecular weights $M_n$ and polydispersity indices were measured by GPC (THF/polystyrene calibration), yields were determined gravimetrically from amount of purified polymer obtained, DP was calculated from the monomer:initiator feed ratio.

| Sample | $[M] \times 10^{-5}$ mol/L | $[I] \times 10^{-6}$ mol/L | DP | $M_{n, calculated}$ g/mol | $M_{n, GPC}$ g/mol | Yield % | PDI |
|---|---|---|---|---|---|---|---|
| 2b | 5.5 | 4.2 | 13 | 46,000 | 20,000 | 90 | 1.14 |
| 2c | 9.7 | 3.5 | 27 | 99,000 | 50,000 | 90 | 1.04 |
| 3a | 3.3 | 4.2 | 8 | 24,000 | 12,000 | 85 | 1.17 |

TABLE 2

Static light and dynamic scattering results for selected samples, dn/dc = 0.13 ml/g (Kwart, et al. J Am Chem Soc 1952, 74, 3094.)

| Sample | $M_w$ g/mol | $A_2 \cdot 10^4$ mol cm³/g² | $R_g$ nm | $R_h$ nm |
|---|---|---|---|---|
| 2b | 56 600 | $-5.62 \cdot 10^{-3}$ | 24 | 9 |
| 3a | 89 900 | $-5.29 \cdot 10^{-2}$ | 66 | 65 |

Example 7

Preparation of Cross-linked Material. In a typical experiment, 0.2 mL of THF (degassed) was added to 0.20 g (55 µmol) of 2, 0.55 µmol of cross-linker (see above) and 1 mg (1.1 µmol) $G_3$ (Scheme 4) were mixed and transferred to an enclosed mold. After 8 hours, the solvent was allowed to evaporate and the material was extracted with THF overnight to remove any sol fraction. The material was dried and ready for use.

Example 8

With reference to the material of Example 7, several representative cross-linked, random copolymers (see below) were prepared using synthetic techniques such as that described above, incorporating cross-linked material at the mole percent shown. The diamine monomer of Example 8a can be prepared in a fashion analogous to that shown in Scheme 2 through reaction of the oxynorbornene anhydride with the corresponding aminoalcohol. Likewise, the tetrahydroxy monomer of Example 8c can be prepared by reacting the anhydride with glycerol. Water absorbency can be defined as the amount of water absorbed by 1 g of the corresponding polymer/copolymer compound.

Superabsorbant Polymers: Swelling Data

Example 8a

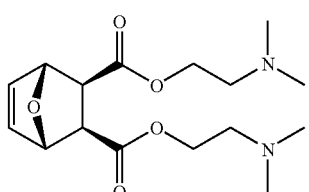

Oxynorbornene-Diamine Monomer

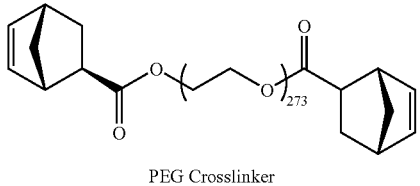

PEG Crosslinker

| Mass of Monomer/ mg | Crosslinker Mol % | Mass of G3/ mg | Gel Dry Mass/mg | Gel Wet Mass/mg | Water Absorbancy |
|---|---|---|---|---|---|
| 50 | 1 | 1.3 | 56 | 4812 | 85 |
| 50 | 2 | 1.3 | 65 | 2509 | 38 |
| 50 | 5 | 1.3 | 108 | 2280 | 20 |
| 50 | 10 | 1.3 | 161 | 2581 | 15 |
| pH = 8.5 | | | | | |
| 50 | 1 | 1.3 | 60 | 12840 | 213 |
| 50 | 2 | 1.3 | 72 | 7419 | 102 |
| 50 | 5 | 1.3 | 128 | 6336 | 49 |
| 50 | 10 | 1.3 | 193 | 5719 | 29 |
| pH = 4.3 | | | | | |
| 50 | 1 | 1.3 | 47 | 2143 | 44 |
| 50 | 2 | 1.3 | 62 | 2138 | 34 |
| 50 | 5 | 1.3 | 103 | 2809 | 26 |
| 50 | 10 | 1.3 | 193 | 4300 | 21 |

0.9 weight % NaCl

Example 8b

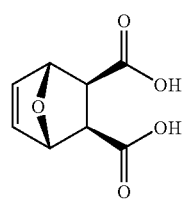

Oxynorbornene-Diacid Monomer

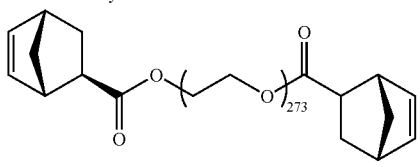

PEG Crosslinker

| Mass of Monomer/mg | Crosslinker Mol % | Mass of G3/mg | Gel Dry Mass/mg | Gel Wet Mass/mg | Water Absorbancy |
|---|---|---|---|---|---|
| 50 | 1 | 2.4 | 27 | 503 | 18 |
| 50 | 2 | 2.4 | 37 | 343 | 8 |
| 50 | 5 | 2.4 | 69 | 886 | 12 |
| 50 | 10 | 2.4 | 93 | 1441 | 15 |
| pH = 8.5 | | | | | |
| 50 | 1 | 2.4 | 27 | 106 | 3 |
| 50 | 2 | 2.4 | 35 | 161 | 4 |
| 50 | 5 | 2.4 | 70 | 625 | 8 |
| 50 | 10 | 2.4 | 81 | 1025 | 12 |
| pH = 4.5 | | | | | |
| 50 | 1 | 2.4 | 13 | 254 | 19 |
| 50 | 2 | 2.4 | 18 | 183 | 9 |

| | | | | | |
|---|---|---|---|---|---|
| pH = 8.5 | | | | | |
| 50 | 1 | 1.4 | 10 | 214 | 20 |
| 50 | 2 | 1.4 | 15 | 290 | 19 |
| 50 | 5 | 1.4 | 18 | 338 | 18 |
| 50 | 10 | 1.4 | 55 | 760 | 13 |
| pH = 4.3 | | | | | |
| 50 | 1 | 1.4 | 14 | 288 | 19 |
| 50 | 2 | 1.4 | 8 | 130 | 15 |
| 50 | 5 | 1.4 | 20 | 364 | 17 |
| 50 | 10 | 1.4 | 60 | 748 | 12 |

0.9 weight % NaCl

Example 8d

| Mol. % | Monomer Mass/g | Cross-Linker Mass/g | G3 Mass/g | THF/mL | Mass before Soxhlet/g | Mass after Soxhlet/g | % Loss | Mass of Wet Gel/g (24 hrs.) | Acid Water absorbency |
|---|---|---|---|---|---|---|---|---|---|
| 0.4 | 0.05 | 0.0072 | 1.3 | 0.5 | 0.057 | 0.048 | 16.1 | 27.641 | 577 |

-continued

| | | | | | |
|---|---|---|---|---|---|
| 50 | 5 | 2.4 | 53 | 596 | 10 |
| 50 | 10 | 2.4 | 145 | 1698 | 11 |

0.9 weight % NaCl

Example 8e

Cross-linked polyacrylic acid

| Dry Mass/g | Wet Mass/g | pH | Water absorbency |
|---|---|---|---|
| 0.05 | 19.02 | 8.3 | 379 |
| 0.05 | 23.46 | 4.9 | 468 |

See FIGS. 7-9 for graphical representations of Swelling Data

What is claimed is:

1. A monomer having Formula I:

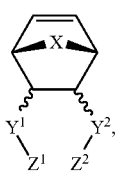

(I)

wherein
X is O, CH$_2$ or substituted CH$_2$;
Y$^1$, Y$^2$ each is carbonyl; and
Z$^1$ is selected from:

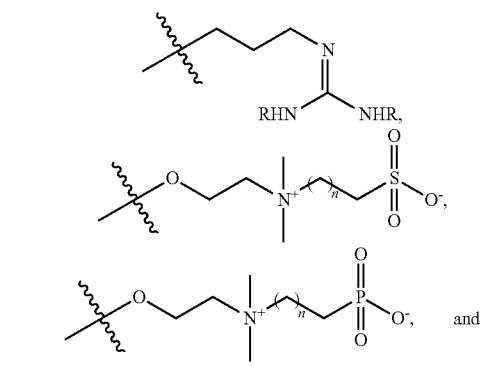

and

Example 8c

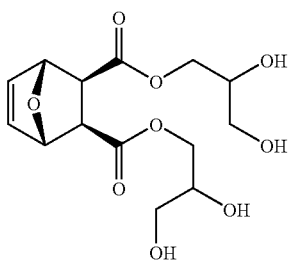

Oxynorbornene-Tetrahydroxy Monomer

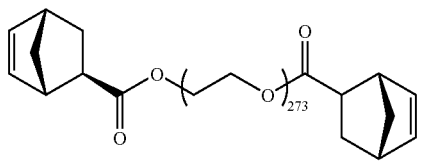

PEG Crosslinker

| Mass of Monomer/mg | Crosslinker Mol % | Mass of G3/mg | Gel Dry Mass/mg | Gel Wet Mass/mg | Water Absorbancy |
|---|---|---|---|---|---|
| 50 | 1 | 1.4 | 22 | 471 | 21 |
| 50 | 2 | 1.4 | 10 | 192 | 18 |
| 50 | 5 | 1.4 | 10 | 144 | 14 |
| 50 | 10 | 1.4 | 56 | 820 | 14 |

-continued
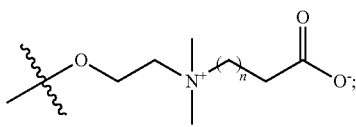
$Z^2$ is selected from:
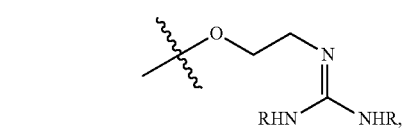
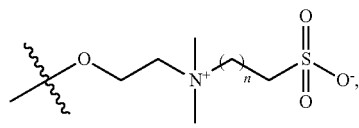
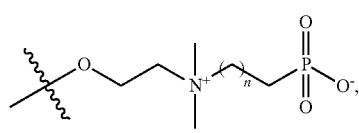
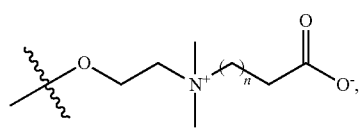
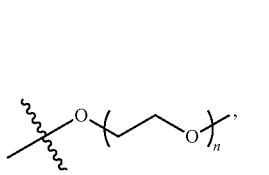 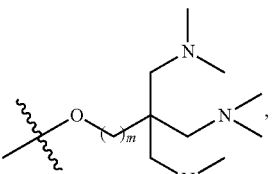
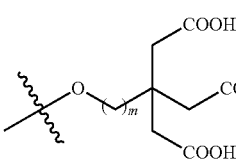 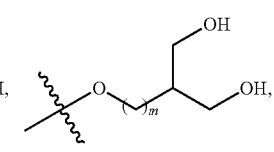
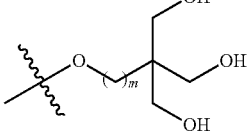 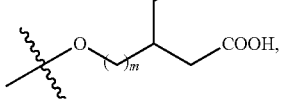
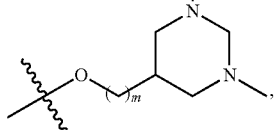 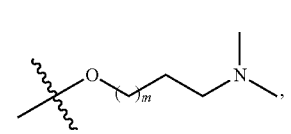
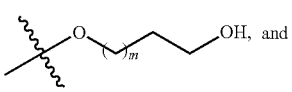 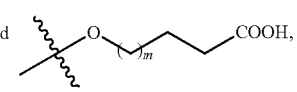
wherein m, n is independently an integer from about 1 to about 50.
2. The monomer of claim 1, wherein $Z^1$ is
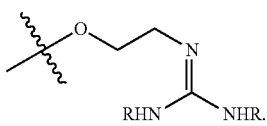
3. The monomer of claim 2, wherein $Z^2$ is selected from:
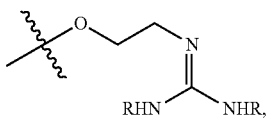
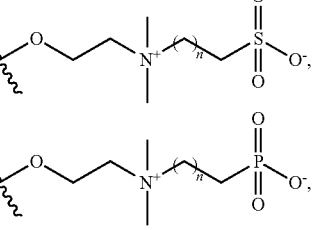
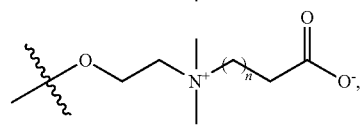
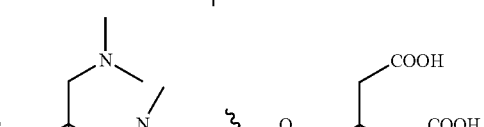
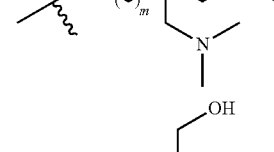 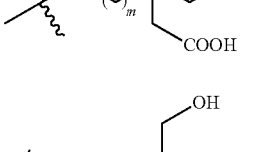
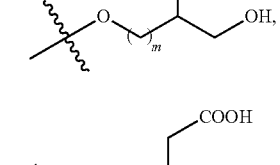 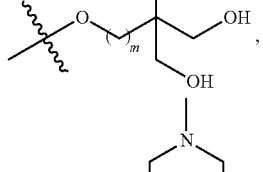
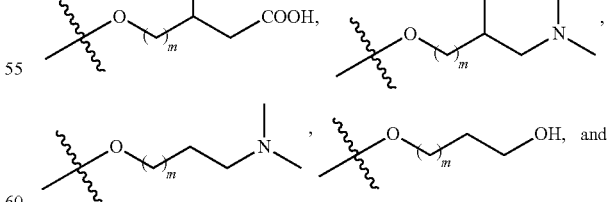
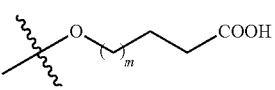
wherein m, n is independently an integer from about 1 to about 50.

4. The monomer of claim 3, wherein $Z^2$ is selected from:

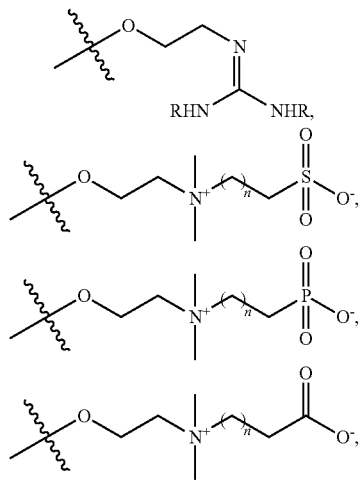

wherein n is independently an integer from about 1 to about 50.

5. The monomer of claim 3, wherein $Z^2$ is selected from:

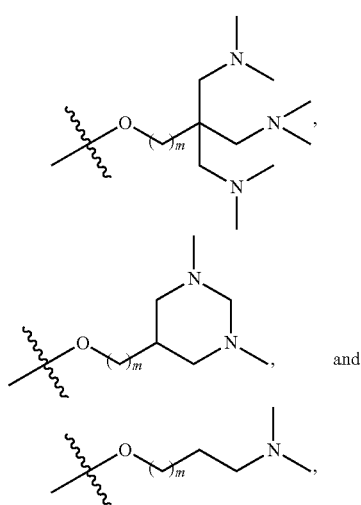

wherein m is independently an integer from about 1 to about 50.

6. The monomer of claim 3, wherein $Z^2$ is selected from:

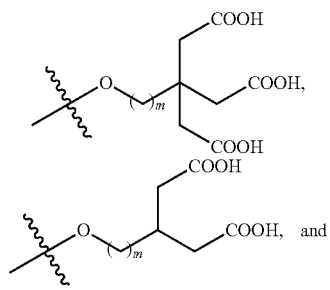

-continued

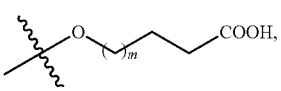

wherein m is independently an integer from about 1 to about 50.

7. The monomer of claim 3, wherein $Z^2$ is selected from:

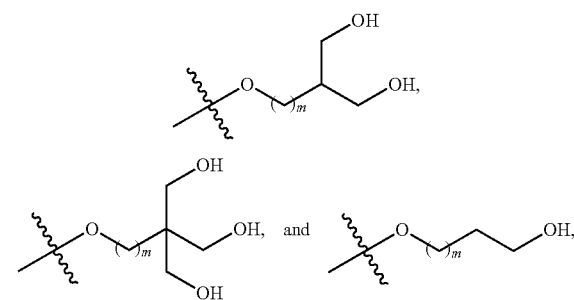

wherein m is independently an integer from about 1 to about 50

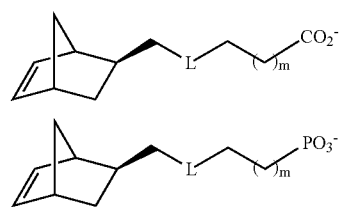

8. The monomer of claim 1, wherein $Z^1$ is selected from:

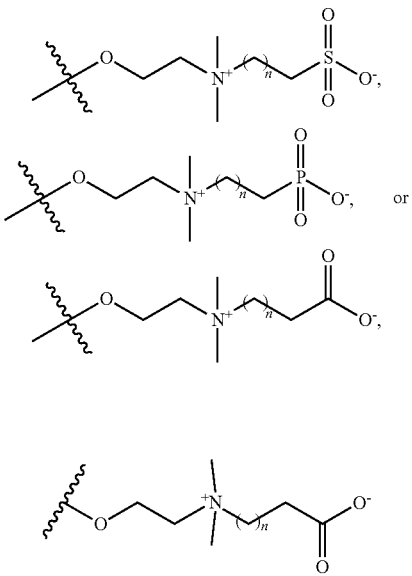

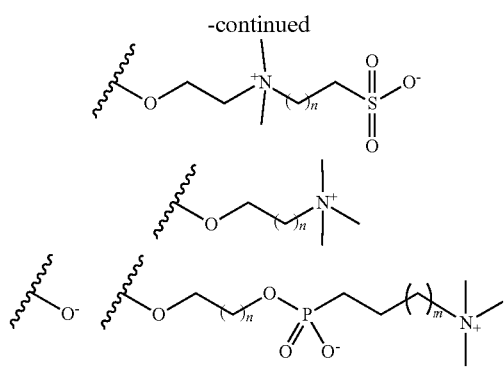

9. The monomer of claim 8, wherein

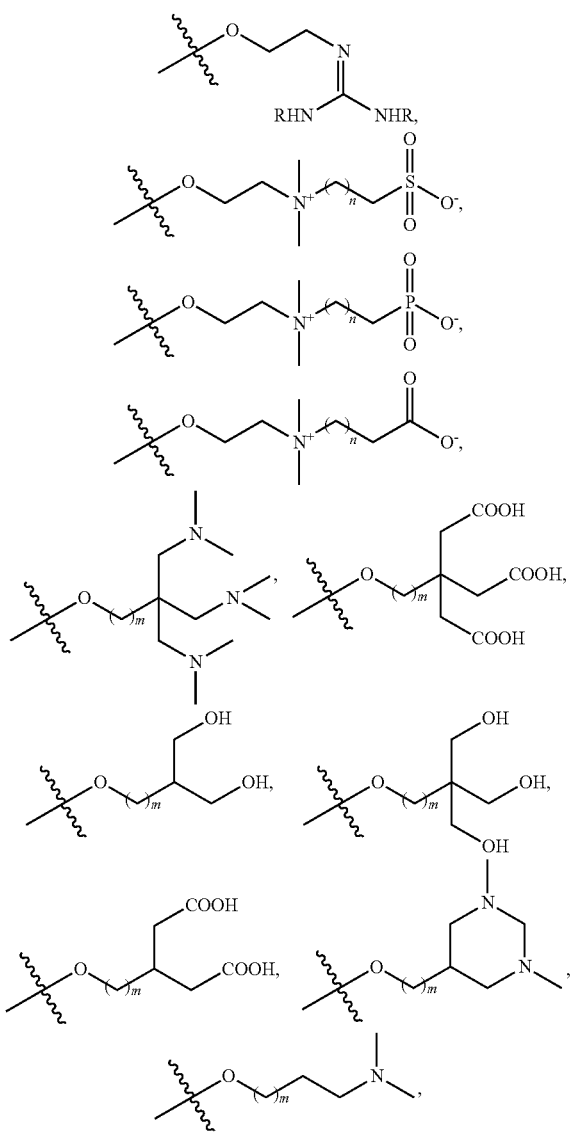

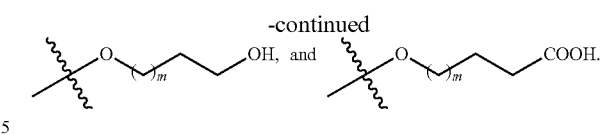

wherein m, n is independently an integer from about 1 to about 50.

10. The monomer of claim 1, wherein each R is independently selected from:

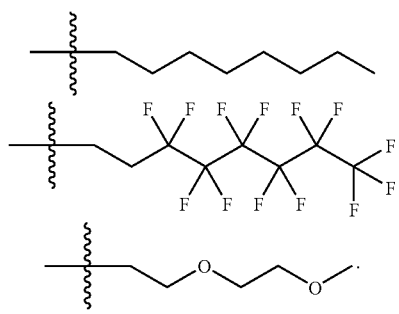

11. The monomer of claim 1, wherein the monomer is capable of crosslinking with a crosslinking agent selected from:

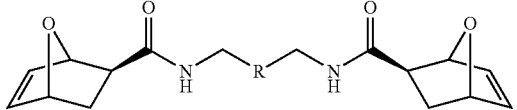

wherein R is —$(CH_2)_m$—, —$(CH_2CH_2O)_n$—, or a peptide of about 3 to about 25 amino acids, m is an integer from about 0 to about 10, and n is an integer from about 1 to about 3000.

12. The monomer of claim 1, wherein the monomer is capable of crosslinking with a crosslinking agent selected from:

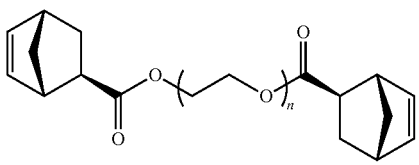

wherein n is from an integer from about 1 to about 3000.

13. The monomer of claim 12, wherein n is from about 100 to about 500.

14. The monomer of claim 13, wherein n is 273.

* * * * *